(12) United States Patent
Kumazawa et al.

(10) Patent No.: US 11,260,085 B2
(45) Date of Patent: Mar. 1, 2022

(54) **SALT-TOLERANT *LACTOBACILLUS*, METHOD OF CULTURING SALT-TOLERANT *LACTOBACILLUS*, AND IMMUNOSTIMULANT**

(71) Applicants: ICHIBIKI CO., LTD., Nagoya (JP); NATIONAL UNIVERSITY CORPORATION TOKYO MEDICAL AND DENTAL UNIVERSITY, Tokyo (JP)

(72) Inventors: Toshihiko Kumazawa, Toyohashi (JP); Atsuhisa Nishimura, Toyohashi (JP); Noriyuki Asai, Toyohashi (JP); Takahiro Adachi, Tokyo (JP)

(73) Assignees: ICHIBIKI CO., LTD., Nagoya (JP); NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 427 days.

(21) Appl. No.: 16/332,577

(22) PCT Filed: Sep. 12, 2017

(86) PCT No.: PCT/JP2017/032933
§ 371 (c)(1),
(2) Date: Mar. 12, 2019

(87) PCT Pub. No.: WO2018/047979
PCT Pub. Date: Mar. 15, 2018

(65) Prior Publication Data
US 2021/0283200 A1    Sep. 16, 2021

(30) Foreign Application Priority Data
Sep. 12, 2016  (JP) .............................. JP2016-178072

(51) Int. Cl.
*A61K 35/744*   (2015.01)
*C07K 14/54*    (2006.01)
*C07K 14/57*    (2006.01)
*C12N 1/20*     (2006.01)
*C12R 1/225*    (2006.01)

(52) U.S. Cl.
CPC ........ *A61K 35/744* (2013.01); *C07K 14/5428* (2013.01); *C07K 14/57* (2013.01); *C12N 1/20* (2013.01); *C12R 2001/225* (2021.05)

(58) Field of Classification Search
None
See application file for complete search history.

(56) References Cited

U.S. PATENT DOCUMENTS

2004/0110270 A1   6/2004  Dennin et al.
2014/0322273 A1*  10/2014 Ai ........................ A61K 31/715
                                            424/234.1

FOREIGN PATENT DOCUMENTS

| CN | 103289927 A | 9/2013 |
|---|---|---|
| JP | 2004-026729 A | 1/2004 |
| JP | 2006-028047 A | 2/2006 |
| JP | 2010-235528 A | 10/2010 |
| JP | 2011-004731 A | 1/2011 |
| JP | 5099649 B2 | 12/2012 |
| JP | 2013-208071 A | 10/2013 |
| JP | 5312322 B2 | 10/2013 |
| WO | 2004/052462 A1 | 6/2004 |

OTHER PUBLICATIONS

Rao et al ( Bioresource Technology 94 (2004) 331-337) (Year: 2004).*
International Search Report dated Dec. 12, 2017, issued for PCT/JP2017/032933.
Supplementary European Search Report dated Apr. 7, 2020, issued for the European Patent Application No. 17848917.5.

* cited by examiner

*Primary Examiner* — Padmavathi Baskar
(74) *Attorney, Agent, or Firm* — Locke Lord LLP

(57) ABSTRACT

There is provided a salt-tolerant *Lactobacillus* having high foodstuff suitability, being easily produced, and having an immunostimulatory action. Salt-tolerant *Lactobacillus* having an immunostimulatory action with viability and activation potency of B cells.

5 Claims, 8 Drawing Sheets

Specification includes a Sequence Listing.

SALT-TOLERANT *LACTOBACILLUS*, METHOD OF CULTURING SALT-TOLERANT *LACTOBACILLUS*, AND IMMUNOSTIMULANT

TECHNICAL FIELD

The present invention relates to a salt-tolerant *Lactobacillus*, a method of culturing a salt-tolerant *Lactobacillus*, and an immunostimulant. More specifically, the present invention relates to a salt-tolerant *Lactobacillus* that has high foodstuff suitability, is easily produced, and has an immunostimulatory action, a method of culturing a salt-tolerant *Lactobacillus*, and an immunostimulant.

BACKGROUND ART

Conventionally, *Lactobacillus* is known to have various actions, and various actions have been reported to include intestinal regulation, improve intestinal flora, reduce cholesterol, reduce an anti-obesity effect, improve a cognitive function effect, have a beauty effect, and the like. Furthermore, the *Lactobacillus* has a number of cases reporting improvement in immunity (allergy improvement, cancer prevention, and infection defense).

In expectation of health effects by the *Lactobacillus*, in the food field, products containing the *Lactobacillus* in various forms such as drinks (beverages), yoghurt, supplements, confectioneries, and the like, are on sale. Further, since the *Lactobacillus* exerts effects in various forms such as viable bacteria, bactericidal bacteria, *Lactobacillus*-producing substances, and the like, the above-described various types of products are present.

Further, as the *Lactobacillus* currently involved in immunity, specifically, (1) "Plasma *Lactobacillus* (*Lactococcus•lactis* JCM 5805 strain)" which directly activates plasmacytoid dendritic cells (pDC) to exhibit antiviral effects, and the like, (2) "1073 R-1 strain (*Lactobacillus bulgaricus* OLL1073R-1)" which has been shown to reduce risk of getting colds due to an effect of enhancing NK activity, (3) "FK-23 bacterium (*Enterococcus faecalis* FK-23)" which is known to activate macrophages and act on intestinal immunity, (4) "L-92 *Lactobacillus* (*Lactobacillus acidophilus* L-92 strain)" (e.g., see Patent Document 1) which directly acts on Th1 and Th2 cells to have a function of controlling IgE antibodies, thereby being demonstrated to be effective against allergic symptoms, and the like, have been reported.

In addition, for example, *Lactobacillus* is involved in fermentation of miso which is a traditional fermented food of Japan. This *Lactobacillus* is a *Lactobacillus* tolerant to sodium chloride, and its main *Lactobacillus* is *Tetragenococcus halophilus*. Historically, Japanese have taken in a salt-tolerant *Lactobacillus* by eating miso.

In addition, *Tetragenococcus halophilus* which is a salt-tolerant *Lactobacillus* is widely and generally isolated from food with a high sodium chloride concentration including carbohydrates such as soy sauce, fish sauce, salted fish, old pickles, and the like, in addition to miso. In addition, particularly in the brewing of soy sauce, *Tetragenococcus halophilus* is used as a starter. As described above, the salt-tolerant *Lactobacillus*, mainly including *Tetragenococcus halophilus*, has long been involved in Japanese diet.

With respect to this salt-tolerant *Lactobacillus*, double-stranded RNA is produced by culturing the salt-tolerant *Lactobacillus* under a salinity stress condition. It has been reported that this double-stranded RNA acts on dendritic cells via Toll-like receptor 3 (TRL 3) and activates immune cells (see Patent Documents 2 and 3).

In addition, as one type of salt-tolerant *Lactobacillus*, a *Lactobacillus* having a potency to induce production of interleukin-12 (IL-12) and interferon-γ (INF-γ), which are Th1-type cytokines, and having a potency to inhibit IgE production has been reported (See Patent Document 4).

CITATION LIST

Patent Documents

| | |
|---|---|
| [Patent Document 1] | JP-A-2004-026729 |
| [Patent Document 2] | JP-B2-5099649 |
| [Patent Document 3] | JP-B2-5312322 |
| [Patent Document 4] | JP-A-2011-004731 |

SUMMARY OF THE INVENTION

Problem to be Solved by the Invention

However, the *Lactobacillus* described in Patent Document 1 have problems in that the growing environment is required to be adjusted sufficiently or equipment such as large-scale tanks that can be sterilized when producing in large quantities is necessary, or labor and cost are required for production such as processing of a culture liquid, or the like.

In addition, since the double-stranded RNAs described in Patent Documents 2 and 3 tend to be damaged due to heating and extinction of *Lactobacillus*, it is necessary to use advanced techniques (for example, it is necessary to control temperature sufficiently to prevent heating at the producing stage and also necessary to use a control device to alleviate the damage of double-stranded RNA due to extinction of *Lactobacillus*) in production at an industrial level.

The salt-tolerant *Lactobacillus* described in Patent Document 4 has a potency to induce production of interleukin-12 and interferon-γ, and the like. Since this salt-tolerant *Lactobacillus* is derived from miso, it is thought that it is easily produced since foodstuff suitability is high and culturing is easy only if there are facilities that can perform sterilization and keep the environment warm.

As described above, salt-tolerant *Lactobacillus* is high in foodstuff suitability and easily produced, and thus if it is possible to find further efficacy and effect of salt-tolerant *Lactobacillus*, a *Lactobacillus* having corresponding efficacy and effect can be easily produced.

The present invention provides a salt-tolerant *Lactobacillus* that exerts an immunostimulatory effect by improving viability and activation potency of B cells by directly acting on B cells.

In addition, the salt-tolerant *Lactobacillus* of the present invention is also easily produced since foodstuff suitability is high (i.e., safety is high) and culturing is easy.

Further, the present invention provides a salt-tolerant *Lactobacillus* having a higher enrichment (proliferation) rate than a salt-tolerant *Staphylococcus* bacterium.

Specifically, in commercial production of *Lactobacillus*, when cultured at a salinity concentration more than 18 w/v %, contaminated bacteria are not be enriched, but the number of culturing days becomes longer, and further, the final yield is lowered (for example, about $1.0 \times 10^9$ cfu/ml). Therefore, a method of culturing at a salinity concentration more than 18 w/v % is not necessarily a condition that it is inexpensive and efficient. Meanwhile, if the salinity concentration is reduced from more than 18 w/v % to 12 to 14 w/v % for the purpose of shortening the number of culturing days and raising the yield, there is a problem in that contaminated bacteria with high salt tolerance (in particular, some of *Staphylococcus* bacteria (salt-tolerant *Staphylococcus* bacteria)) proliferate.

Therefore, it is desired to find salt-tolerant *Lactobacillus* (genus *Tetragenococcus*) which has a faster enrichment rate than that of the salt-tolerant *Staphylococcus* bacteria at a salinity concentration of 18 w/v % or less such as 12 to 14 w/v %.

Means for Solving the Problem

According to the present invention, a salt-tolerant *Lactobacillus*, a method of culturing a salt-tolerant *Lactobacillus*, and an immunostimulant are provided as follows:

[1] A salt-tolerant *Lactobacillus* having an immunostimulatory action with viability and activation potency of B cells.

[2] The salt-tolerant *Lactobacillus* described in [1], wherein the salt-tolerant *Lactobacillus* is isolated in a brewing process of miso.

[3] The salt-tolerant *Lactobacillus* described in [1] or [2], wherein the salt-tolerant *Lactobacillus* is a salt-tolerant *Lactobacillus* of Accession number NITE BP-02318, a salt-tolerant *Lactobacillus* of Accession number NITE BP-02319, a salt-tolerant *Lactobacillus* of Accession number NITE BP-02320, a salt-tolerant *Lactobacillus* of Accession number NITE BP-02321, a salt-tolerant *Lactobacillus* of Accession number NITE BP-02322, a salt-tolerant *Lactobacillus* of Accession number NITE BP-02323, or a salt-tolerant *Lactobacillus* of Accession number NITE BP-02324.

[4] The salt-tolerant *Lactobacillus* described in any one of [1] to [3], wherein production of interleukin-22, interleukin-10, and interferon-γ is induced.

[5] A method of culturing a salt-tolerant *Lactobacillus* in which the salt-tolerant *Lactobacillus* described in any one of [1] to [4] is cultured in a medium having a salinity concentration of 11 to 18 w/v %.

[6] An immunostimulant containing the salt-tolerant *Lactobacillus* described in any one of [1] to [4].

Effect of the Invention

The salt-tolerant *Lactobacillus* of the present invention is easily produced since foodstuff suitability (e.g., capable of being produced by a *Lactobacillus* derived from miso) is high (i.e., safety is high) and culturing is easy, and also has an immunostimulatory action.

According to the method of culturing a salt-tolerant *Lactobacillus* of the present invention, the salt-tolerant *Lactobacillus* of the present invention can be easily and well cultured.

The immunostimulant of the present invention is easily produced since foodstuff suitability (e.g., capable of being produced by a *Lactobacillus* derived from miso) is high (i.e., safety is high) and culturing is easy, and also has an immunostimulatory action.

MODE FOR CARRYING OUT THE INVENTION

Figure 1:
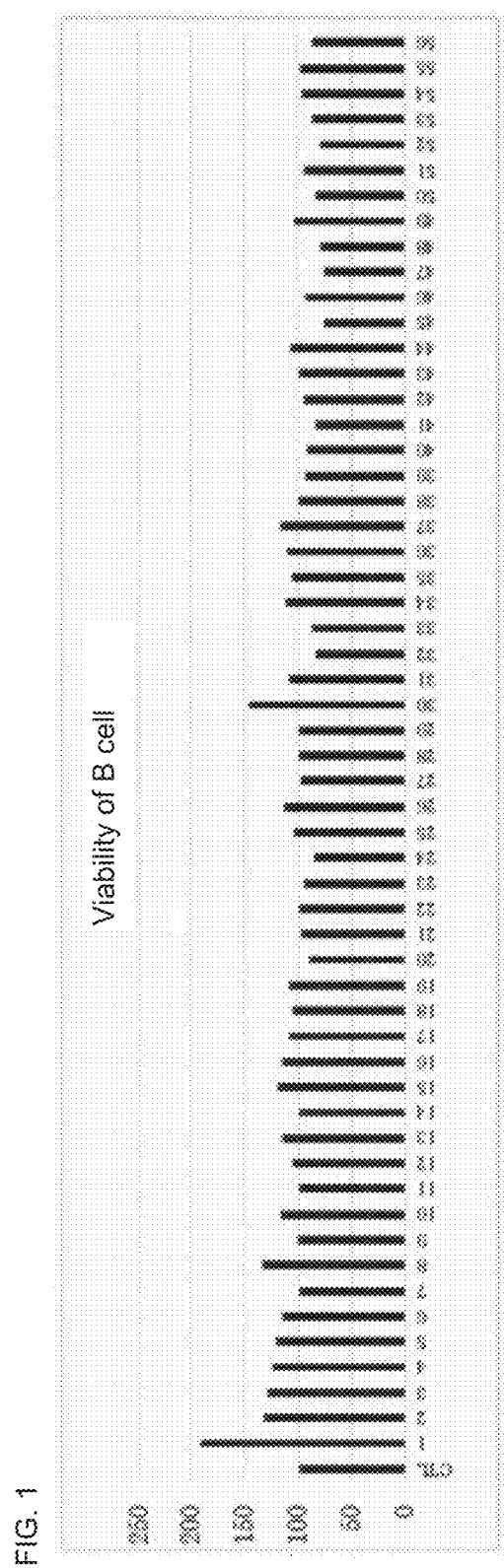
FIG. 1 is a graph showing results of viability of spleen B cells in Example 1.

Hereinafter, modes for carrying out the present invention will be described, but the present invention is not limited to the following embodiments. That is, it should be understood that those in which changes, improvements, and the like, have been appropriately added to the following embodiments based on the ordinary knowledge of those skilled in the art without departing from the gist of the present invention fall within the scope of the present invention.

[1] Salt-Tolerant *Lactobacillus*

The salt-tolerant *Lactobacillus* of the present invention has viability and activation potency of B cells. The salt-tolerant *Lactobacillus* of the present invention can be isolated, for example, in a brewing process of miso. In addition, the salt-tolerant *Lactobacillus* of the present invention can be *Tetragenococcus halophilus*.

The salt-tolerant *Lactobacillus* is easily produced since safety is high (i.e., foodstuff suitability is high) and culturing is easy, and acts directly on B cells to improve viability and activation potency in B cells, thereby activating an immune system (i.e., having immunostimulatory action). In addition, according to the related art, among the salt-tolerant lactobacilli, *Lactobacillus* acting on lymphocyte T cells or dendritic cells is known.

Here, B cells play a central role in humoral immunity and are the only cells capable of producing antibodies against foreign bodies (antigens) such as pathogens, but is little known about an action of *Lactobacillus*. In addition, B cells, which are cells that present antigen to T cells, are known to be indispensable cells for maintenance of activated T cells. Therefore, strengthening the action of B cells reinforces an action of T cells, and also strengthens an immunostimulatory effect in the entire cells of the immune system. In the present invention, "activation potency of B cell" means that both a potency of antibody production and a potency of antigen presentation are activated.

In addition, if it is possible to achieve a direct control such as artificial reinforcement of action of B cells capable of producing antibodies to attack foreign bodies, it can be expected to lead to prevention, alleviation, or treatment of immune system diseases such as allergic diseases, infectious diseases, and autoimmune diseases having an effect on the action by the antibody.

In the present specification, the term "having viability of B cells" means that when a ratio of the number of viable B cells to the total number of cells in a sample to which no *Lactobacillus* is added using B cells (spleen B cells) isolated from the experimental mouse spleen cells is set as a reference (reference value 100), a value (measured value) of the ratio of the number of viable B cells to the total number of cells in the sample to which the *Lactobacillus* is added is more than 100 (provided that the reference value and the measured value are values obtained by subtracting a standard error from the mean value, respectively). Cells that react with an anti-B220 antibody are referred to as B cells, and the "total number of cells" can be quantitatively determined by flow cytometry. The "number of viable B cells (living cells)" is a value obtained by subtracting the number of cells (dead cells) stained with propidium iodide (PI) nucleus staining liquid from the total number of cells.

In addition, the description "having viability of B cells" is the same as described above, but specifically, means that a value (measured value) obtained by a method shown in Example 1 (i.e., in a sequence of "viability of B cell" including (2) preparation of B cells, (3) cell culture, and (4) measurement of viability and activation potency of B cells) is more than 100.

In the present specification, the term "having an activation potency of B cells" means that when a ratio of the number of activated B cells to the number of unactivated B cells in a sample to which no *Lactobacillus* is added using B cells (spleen B cells) isolated from spleen cells is set as a reference (reference value 100), a value (measured value) of the ratio of the number of activated B cells to the number of unactivated B cells in the sample to which the *Lactobacillus* is added is more than 100 (provided that the reference value and the measured value are values obtained by subtracting a standard error from the mean value, respectively). Further, the "number of activated B cells" may be determined by measuring the number of cells reacting with both anti-B220 antibody and anti-CD86 antibody by flow cytometry. Further, "the number of unactivated B cells" may be determined by measuring the number of cells reacting with anti-B220 antibody without reacting with anti-CD86 antibody by flow cytometry. In addition, it is assumed that these cells are living cells (cells not stained with PI).

In addition, the description "having activation potency of B cells" is the same as described above, but specifically, means that a value (measured value) obtained by a method shown in Example 1 (i.e., in a sequence of "activation potency of B cell" including (2) preparation of B cells, (3) cell culture, and (4) measurement of viability and activation potency of B cells) is more than 100.

In addition, the salt-tolerant *Lactobacillus* "isolated in the brewing process of miso" refers to a salt-tolerant *Lactobacillus* established in "storage", "chamber", "tub", and the like, in the miso brewing process. In addition, the *Lactobacillus* refers to a bacterium that can proliferate from addition of miso to an aging process. This salt-tolerant *Lactobacillus* "isolated in the brewing process of miso" can be called a salt-tolerant *Lactobacillus* contained in miso (i.e., miso *Lactobacillus*), and in other words, a salt-tolerant *Lactobacillus* derived from miso (i.e., salt-tolerant *Lactobacillus* originating from miso). In addition, in the present invention, the "salt-tolerant *Lactobacillus* isolated in the brewing process of miso" is not limited to the bacterium isolated in the brewing process of miso, but includes bacterium that is isolated in the brewing process of the miso, and then cultured (subcultured).

Conventionally, it has been known that *Lactobacillus* has an immunostimulatory action even if it is a dead cell, and products utilizing this action (immunostimulatory potency) have been widely developed.

This *Lactobacillus* has advantages in that it is easy to concentrate *Lactobacillus* by centrifugation, drying, or the like, it is easy to stabilize the number of bacteria, handling is relatively easy, and the like.

In order to actually obtain the immunostimulatory effect, it is necessary to ingest a large amount of bacterial cells, but in order to prepare the large amount of bacterial cells, a large scale tank for culturing becomes essential, and thus high capital equipment is required. Further, there are problems that it is necessary to perform treatment of the culture liquid such as a concentration treatment and purification treatment of the cells, and to perform considerable sterilization in the autoclave, and the like.

Therefore, the present inventors conducted intensive studies on *Lactobacillus* capable of having high foodstuff suitability, being easily produced, and capable of stimulating immunity. In addition, the present inventors focused on effectiveness of the salt-tolerant *Lactobacillus* (for example, those isolated in the brewing process of miso) capable of having high foodstuff suitability, being mass-produced by a simple culture facility, and being simply produced.

Further, the present inventors have found that, if it is possible to improve the viability and activation potency of B cells that produce antibodies required for biological defense using the salt-tolerant *Lactobacillus*, the immune system can be activated, and the *Lactobacillus* may effectively act on the immune response, which is very useful.

In other words, salt-tolerant *Lactobacillus* is contained in foods such as miso and soy sauce, and the like, and thus foodstuff suitability is high. In addition, as the salt-tolerant *Lactobacillus* of the present invention, for example, a bacterium isolated in the brewing process of miso (miso *Lactobacillus*) can be used, and this miso *Lactobacillus* also has high foodstuff suitability. In addition, the salt-tolerant *Lactobacillus* of the present invention can be cultured in a medium having a high salinity concentration, and can easily grow in an environment where it is difficult for contaminated bacteria to proliferate as shown by a culturing method described below. More preferably, if a salt-tolerant *Lactobacillus* has a higher enrichment rate as compared to salt-tolerant *Staphylococcus* bacteria, the number of culturing days can be shortened as compared with a case where a salinity concentration increases (salinity concentration exceeding 18 w/v %), and can increase the final yield. As a result, it is possible to produce salt-tolerant *Lactobacillus* more efficiently in a large amount by a simple culture facility, and thus it is possible to reduce the capital investment in the culture apparatus as compared with the culture of general *Lactobacillus*.

More specifically, the salt-tolerant *Lactobacillus* of the present invention may have a larger proliferation factor than that of the salt-tolerant *Staphylococcus* bacterium (SN-2820 strain). In this case, the number of culturing days can be shortened and the final yield can be increased. As a result, it is possible to produce salt-tolerant *Lactobacillus* more efficiently in a large amount by a simple culture facility, and thus it is possible to reduce the capital investment in the culture apparatus as compared with the culture of general *Lactobacillus*. Further, in the present specification, the "proliferation factor" means a value calculated by expression: "number of bacteria after culturing for 20 hours (cfu/ml)/number of initial bacteria (cfu/ml)" when culturing under the condition of Example 4.

Here, immune cells are responsible for the body's defense system, which is the immune system, against external pathogens. In addition, a main body of immune cells is leukocytes, and the leukocytes are composed of macrophages, lymphocytes, and granulocytes. In these cells, the lymphocytes play a central role in immune function, and are composed of T cells, B cells, NK cells (natural killer cells) and cells that play important roles, respectively. In lymphocyte cells, B cells are the only cells that produce antibodies necessary to eliminate pathogens that enter the body, and play a central role in humoral immunity. In addition, B cells are also known to be one of antigen-presenting cells that transmit antigen information to T cells.

The salt-tolerant *Lactobacillus* of the present invention may be any bacterium as long as it has viability and activation potency of B cells. For example, the salt-tolerant *Lactobacillus* of the present invention can be a *Tetragenococcus halophilus* isolated in the brewing process of miso.

The salt-tolerant *Lactobacillus* of the present invention is preferably a *Lactobacillus* having a low histamine-producing potency It is also preferred that the salt-tolerant *Lactobacillus* of the present invention induces production of interleukin-22, interleukin-10, and interferon-γ. Since the salt-tolerant *Lactobacillus* of the present invention induces the production of interleukin-22, keratinized cells proliferate to promote turnover of the skin, and thus the salt-tolerant *Lactobacillus* can be expected to be suitably used for skin care materials, antibacterial materials, and the like. Interleukin-22 is a cytokine belonging to the interleukin-10 family, and is involved in mucosal barrier protection of the skin and intestinal tract, tissue repair, and cell survival and proliferation, and it can be expected to have usages such as prevention and treatment, and the like, of skin diseases such as atopic dermatitis, and the like, fatty liver disease, infectious diseases caused by *Clostridium difficile* (*C. difficile*), and the like.

In particular, it is preferred that the salt-tolerant *Lactobacillus* of the present invention induces production of interleukin-22, interleukin-10, and interferon-γ from B cells. Interferon-γ is known to enhance cellular immunity of killer T cells or macrophages that attack viruses, and the like, and to act on immunostimulation. Interleukin-10 is a potent anti-inflammatory cytokine and produced by a regulatory B cell among B cells. It has been reported that this regulatory B cell has an inhibitory potency against inflammation, autoimmune disease, infectious immunity, and the like, and has a function (immune tolerance) that inhibits an inappropriate immune reaction. Thus, by stimulating B cells with the salt-tolerant *Lactobacillus* of the present invention, production of various cytokines such as interleukin-22, interleukin-10, and interferon-γ is induced, and as a result, there is an advantage that biological defense is enhanced since the immune response is enhanced.

[1-1] Preferable Salt-Tolerant *Lactobacillus*:

The salt-tolerant *Lactobacillus* of the present invention is preferably at least one selected from the group consisting of a salt-tolerant *Lactobacillus* of Accession number NITE BP-02318 (hereinafter sometimes referred to as "strain No. 1" or simply "No. 1"), a salt-tolerant *Lactobacillus* of Accession number NITE BP-02319 (hereinafter sometimes referred to as "strain No. 3" or simply "No. 3"), a salt-tolerant *Lactobacillus* of Accession number NITE BP-02320 (hereinafter sometimes referred to as "strain No. 13" or simply "No. 13"), a salt-tolerant *Lactobacillus* of Accession number NITE BP-02321 (hereinafter sometimes referred to as "strain No. 15" or simply "No. 15"), a salt-tolerant *Lactobacillus* of Accession number NITE BP-02322 (hereinafter sometimes referred to as "strain No. 19" or simply "No. 19"), a salt-tolerant *Lactobacillus* of Accession number NITE BP-02323 (hereinafter sometimes referred to as "strain No. 30" or simply "No. 30"), and a salt-tolerant *Lactobacillus* of Accession number NITE BP-02324 (hereinafter sometimes referred to as "strain No. 31" or simply "No. 31"). In addition, the salt-tolerant *Lactobacillus* of the present invention is the salt-tolerant *Lactobacillus* of Accession number NITE BP-02318, the salt-tolerant *Lactobacillus* of Accession number NITE BP-02319, the salt-tolerant *Lactobacillus* of Accession number NITE BP-02320, the salt-tolerant *Lactobacillus* of Accession number NITE BP-02321, the salt-tolerant *Lactobacillus* of Accession number NITE BP-02322, the salt-tolerant *Lactobacillus* of Accession number NITE BP-02323, or the salt-tolerant *Lactobacillus* of Accession number NITE BP-02324.

These salt-tolerant lactobacilli are, for example, lactobacilli derived from miso (i.e., miso *Lactobacillus*), and thus these are highly safe and easily produced due to easy growth, and further these lactobacilli may act directly on B cells to realize the viability and the activation potency in B cells, thereby stimulating an immune system better (i.e., better immunostimulatory action). The above-described salt-tolerant *Lactobacillus* can also act on T cells, and it is also thought to act on dendritic cells and the like. In addition, the salt-tolerant *Lactobacillus* can increase IgA (Immunoglobulin A) concentration in the serum, and can improve the immunostimulatory potency. In addition, the above described salt-tolerant lactobacilli of strains Nos. 1, 3, 13, 15, 19, 30, and 31 are *Tetragenococcus halophilus*.

In addition, the salt-tolerant *Lactobacillus* of Accession number NITE BP-02318, the salt-tolerant *Lactobacillus* of Accession number NITE BP-02319, the salt-tolerant *Lactobacillus* of Accession number NITE BP-02320, the salt-tolerant *Lactobacillus* of Accession number NITE BP-02321, the salt-tolerant *Lactobacillus* of Accession number NITE BP-02322, the salt-tolerant *Lactobacillus* of Accession number NITE BP-02323, and the salt-tolerant *Lactobacillus* of Accession number NITE BP-02324 are deposited with the National Institute of Technology and Evaluation (NITE) Patent Microorganisms Depositary (NPMD).

Among "preferable salt-tolerant lactobacilli", the salt-tolerant lactobacilli of strain No. 1, strain No. 13, strain No. 19, and strain No. 30 are generally excellent in viability of each cell (including B cells and T cells) (see Example 2). Therefore, according to the salt-tolerant lactobacilli of strain No. 1, strain No. 13, strain No. 19, and strain No. 30, an immunostimulatory action is exerted by increasing the total number of immune cells, and thus these lactobacilli can be suitably used as an active ingredient of an immunostimulant.

Among "preferable salt-tolerant lactobacilli", the salt-tolerant lactobacilli of strain No. 1, and strain No. 31 are generally excellent in viability of B cell and activation potency of B cells. In particular, the salt-tolerant *Lactobacillus* of strain No. 31 has very high activation potency of B cells. In addition, the salt-tolerant lactobacilli of strain No. 1 and No. 31 may be used as an active ingredient of highly efficient immunostimulant.

The salt-tolerant *Lactobacillus* of the present invention is preferably any one selected from salt-tolerant lactobacilli of strain No. 1, strain No. 3, strain No. 13, strain No. 15, strain No. 30, and strain No. 31. These salt-tolerant lactobacilli have a short number of culturing days and a high final yield. More specifically, the salt-tolerant lactobacilli may have a larger proliferation factor than that of the salt-tolerant *Staphylococcus* bacterium (SN-2820 strain). Therefore, as compared with the salt-tolerant *Lactobacillus* of strain No. 19, the number of culturing days can be shortened and the final yield is high. As a result, it is possible to achieve production more efficiently and in large quantities with simpler culture facility. In addition, among the salt-tolerant lactobacilli of strains Nos. 1, 3, 13, 15, 19, 30, and 31, a bacterium having a very excellent immunostimulatory effect and being suitable for production in simple culture facility is a strain-tolerant *Lactobacillus* of strain No. 1.

[1-1a] Salt-Tolerant *Lactobacillus* of Accession Number NITE BP-02318:

The salt-tolerant *Lactobacillus* of Accession number NITE BP-02318 (strain No. 1) is very excellent in both the viability of B cell and the activation potency of B cells. Therefore, according to the salt-tolerant *Lactobacillus* of strain No. 1, very good immunostimulatory action is exerted.

Further, this salt-tolerant *Lactobacillus* of strain No. 1 is excellent in potency to induce production of interleukin-22, interleukin-10, and interferon-γ. This salt-tolerant *Lactobacillus* of strain No. 1 is excellent in potency to induce production of interleukin-22, and thus keratinocytes proliferate to promote skin turnover as described above. Therefore, the salt-tolerant *Lactobacillus* of strain No. 1 can be preferably used for applications such as skin materials, antibacterial material, and the like. In addition, the salt-tolerant lactobacilli of strains Nos. 3, 13, 15, 19, 30, and 31 also may have excellent potency to induce production of interleukin-22 to be preferably used for applications such as skin materials, antibacterial material, and the like, similar to the salt-tolerant *Lactobacillus* of strain No. 1.

In particular, the salt-tolerant *Lactobacillus* of strain No. 1 is excellent in potency to induce production of interleukin-10 among potencies to induce production of interleukin-22, interleukin-10, and interferon-γ, whereas weak potency to induce production of interferon-γ among them (see FIGS. 9 to 14). Therefore, when it is attempted to produce a large amount of interleukin-10 among interleukin-22, interleukin-10, and interferon-γ, it is considered that it is very effective to utilize the salt-tolerant *Lactobacillus* of strain No. 1. Here, in the immune system, it is an important factor that both the immunostimulatory potency and the immune tolerance function work well in balance. From this viewpoint, according to the salt-tolerant *Lactobacillus* of strain No. 1, the immunostimulatory potency may be improved by interferon-γ, and meanwhile, a function of inhibiting an inappropriate immune reaction (tolerance to immunity) may be exerted by interleukin-10 and interleukin-22 belonging to the interleukin-10 family, and thus both the immunostimulatory potency and the immune tolerance function work in a balanced manner overall. In this way, using the salt-tolerant *Lactobacillus* of strain No. 1, not only interleukin-22 and interferon-γ but also interleukin-10 which is a cytokine with potent anti-inflammatory effect, will work sufficiently. As a result, it is expected that the immune system as a whole will function in a well-balanced manner and enhance the proper immune response function against pathogens and the like.

Figure 18:
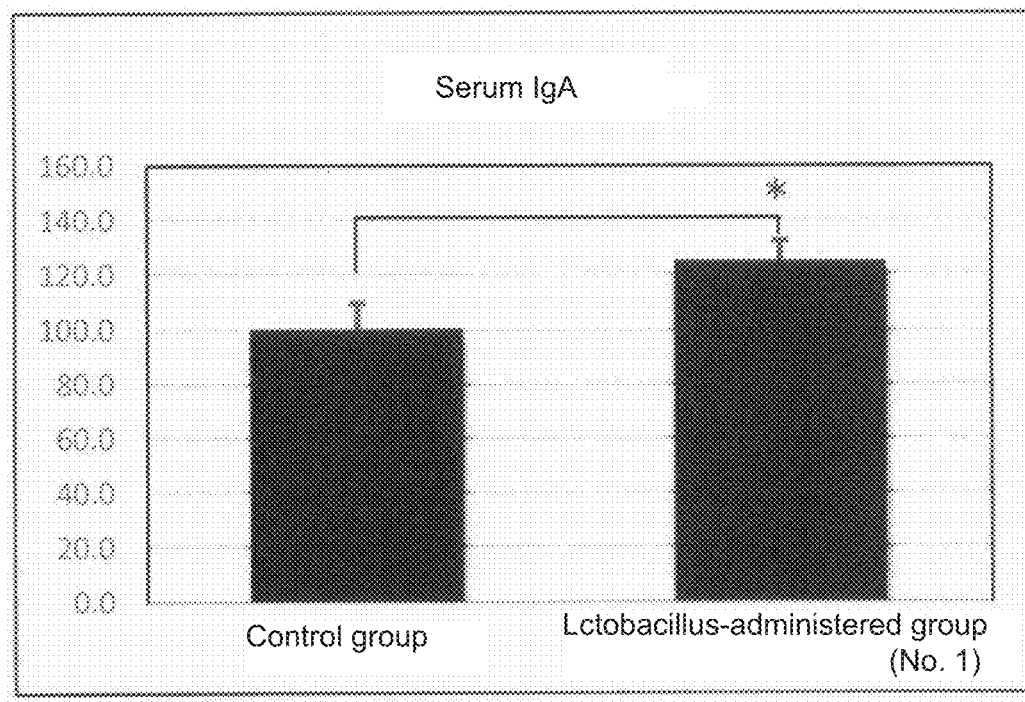
FIG. 18 is a graph showing measurement results of serum IgA of mice in Example 6.

The salt-tolerant *Lactobacillus* of strain No. 1 can increase a concentration of IgA (Immunoglobulin A) in the serum (see Table 7 and FIG. 18). Since this IgA is involved in local immunity on the mucosal surface, for example, by using the salt-tolerant *Lactobacillus* of strain No. 1, IgA concentration can also increase and immunostimulatory potency can be improved.

The salt-tolerant *Lactobacillus* of strain No. 1 does not directly affect the expression of interleukin-12 via B cell. That is, the salt-tolerant *Lactobacillus* of strain No. 1 does not have the potency to induce production of interleukin-12 via B cells (see Table 3).

[1-1b] Salt-tolerant *Lactobacillus* of Accession numbers NITE BP-02319 to BP-02322:

With respect to the salt-tolerant *Lactobacillus* of Accession numbers NITE BP-02319 to BP-02322 (strain No. 3, strain No. 13, strain No. 15, and strain No. 19), potency to induce production of interleukin-22, interleukin-10, and interferon-γ is excellent. In particular, these salt-tolerant lactobacilli are excellent in potency to induce production of interferon-γ among potencies to induce production of interleukin-22, interleukin-10, and interferon-γ. Therefore, when it is attempted to produce a large amount of interferon-γ among interleukin-22, interleukin-10, and interferon-γ, it is effective to utilize these salt-tolerant lactobacilli. Since the interferon-γ has an action of promoting proliferation of NK cells and increasing offense power of NK cells, when it is attempted to enhance the action of interferon-γ, these salt-tolerant lactobacilli of these strains can be employed.

[1-1c] Salt-tolerant *Lactobacillus* of Accession number NITE BP-02323:

The salt-tolerant *Lactobacillus* of Accession number NITE BP-02323 (strain No. 30) is also excellent in the potency to induce production of interleukin-22, interleukin-10, and interferon-γ. In particular, the salt-tolerant *Lactobacillus* of strain No. 30 is excellent in potency to induce production of interferon-γ among potencies to induce production of interleukin-22, interleukin-10, and interferon-γ.

Figure 19:
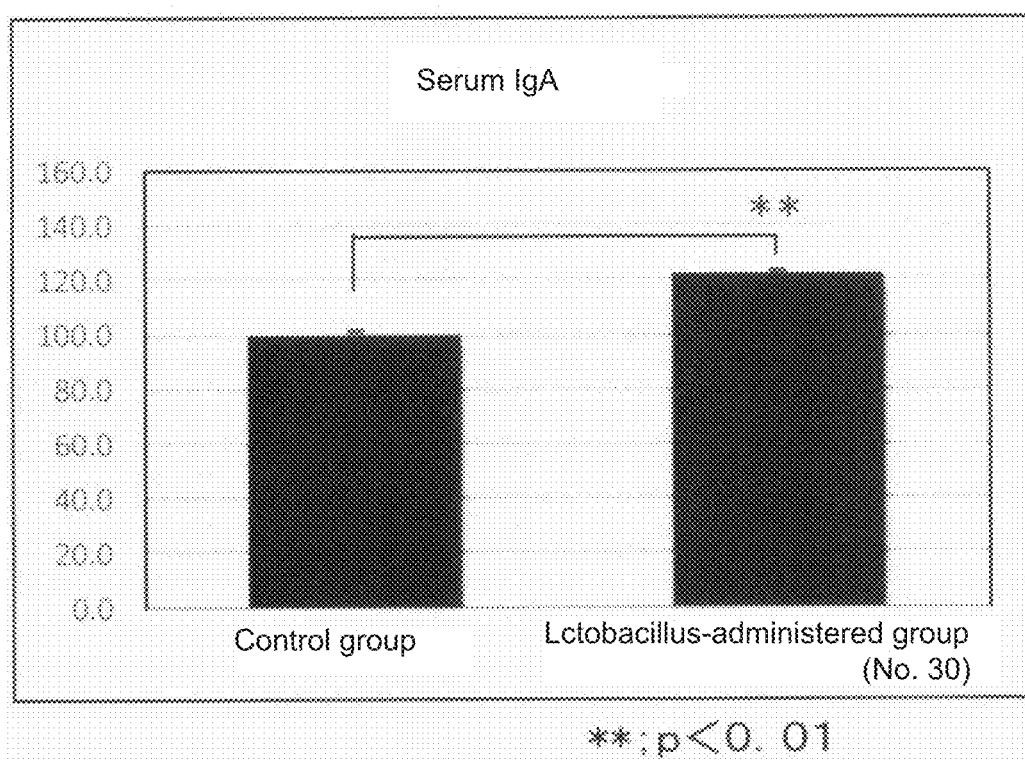
FIG. 19 is a graph showing the measurement results of serum IgA of mice in Example 6.

Further, this salt-tolerant *Lactobacillus* of strain No. 30 can increase IgA concentration in serum (see Table 8, FIG. 19). For example, by using the salt-tolerant *Lactobacillus* of strain No. 30, it is possible to increase IgA concentration as well as to improve immunostimulatory potency.

It is considered that it is effective to use the salt-tolerant *Lactobacillus* of strain No. 30 in cases where it is attempted to increase the concentration of IgA in serum as well as produce interferon-γ largely among interleukin-22, interleukin-10, and interferon-γ.

[1-1d] Salt-Tolerant *Lactobacillus* of Accession Number NITE BP-02324:

The salt-tolerant *Lactobacillus* of Accession number NITE BP-02324 (strain No. 31) is very excellent in the potency to induce production of interleukin-22, interleukin-10, and interferon-γ. That is, it is considered that it is effective to use the salt-tolerant *Lactobacillus* of strain No. 31 in cases where it is attempted to produce all of interleukin-22, interleukin-10, and interferon-γ largely.

[2] Method of Culturing Salt-Tolerant *Lactobacillus*:

In the method of culturing a salt-tolerant *Lactobacillus* of the present invention, the salt-tolerant *Lactobacillus* of the present invention is cultured in a medium having a salinity concentration of 11 to 18 w/v %. In addition, "w/v %" means (mass (g)/volume (100 mL))%.

By culturing under such conditions, it is possible to culture the salt-tolerant *Lactobacillus* of the present invention simply and well. Specifically, in commercial production of *Lactobacillus*, when cultured at a salinity concentration of more than 18 w/v %, contaminated bacteria are not be enriched, but the number of culturing days becomes longer, and further, the final yield is lowered (for example, about $1.0 \times 10^9$ cfu/ml). Therefore, a method of culturing at a salinity concentration more than 18 w/v % is not necessarily a condition that it is inexpensive and efficient. Meanwhile, if the salinity concentration of the medium is reduced from more than 18 w/v % to 12 to 14 w/v % for the purpose of shortening the number of culturing days and raising the yield, there is a problem in that contaminated bacteria with high salt tolerance (in particular, some of *Staphylococcus* bacteria (salt-tolerant *Staphylococcus* bacteria)) is proliferated.

Therefore, by culturing the salt-tolerant *Lactobacillus* of the present invention in the medium having the salinity concentration, it is possible to prevent enrichment for contaminated bacteria not having salt tolerance, and on the other hand, to terminate the culturing before contaminated bacteria having salt tolerance are enriched since an enrichment rate is faster than that of the salt-tolerant *Streptococcus* sp. bacterium. Therefore, according to the culturing method of the present invention, it is possible to produce salt-tolerant *Lactobacillus* more efficiently in a large amount by a simple culture facility, and thus it is possible to reduce the capital investment in the culture apparatus as compared with the culture of general *Lactobacillus*.

As a medium, a medium containing a nitrogen source and a carbon source can be used.

The nitrogen source is not particularly limited, and examples thereof may include soy sauce, miso, meat extract, peptone, gluten, casein, yeast extract, amino acid, and the like. In addition, the carbon source is not particularly limited, and examples thereof may include glucose, malted rice, saccharification liquid of rice, sucrose, starch, powder candy, glycerin, and the like. Further, in addition to the nitrogen source and the carbon source, inorganic salts such as sodium acetate, magnesium, manganese, iron, and the like may be contained as inorganic materials, and the like may be contained, and vitamins may be contained.

A salinity concentration of the medium is preferably 11 to 18 w/v %, more preferably 11 to 16 w/v %, and particularly preferably 12 to 14 w/v %. When the salinity concentration of the medium exceeds 18 w/v %, the salt-tolerant *Lactobacillus* proliferates more vigorously than bacteria (contaminated bacteria). However, when the salinity concentration exceeds 18 w/v %, the proliferation rate of the salt-tolerant *Lactobacillus* becomes slow as compared with the other salinity concentrations, and the final yield decreases.

A culture temperature is preferably 20 to 40° C., and more preferably 28 to 37° C. A culturing time is about 24 to 120 hours, and stirring may be performed during culturing. In addition, the pH of the medium is preferably 5 to 9, and more preferably 6 to 7.

According to the present method, sodium chloride is included at a high concentration in the medium, and thus it is difficult for contaminated bacteria such as *Escherichia coli*, soil bacteria, and the like, to be enriched. Here, if the salinity concentration of the medium is lowered from 18 w/v % to 12 to 14 w/v % in order to shorten the culture time and increase the final yield, there is a possibility that the salt-tolerant *Staphylococcus* bacterium is enriched. However, even if the salinity concentration is lowered, if the enrichment rate of the *Lactobacillus* is faster than that of the salt-tolerant *Staphylococcus* bacterium, the medium is not affected by contaminated bacteria. According to the method of the present invention, it is possible to culture a salt-tolerant *Lactobacillus* easily and satisfactorily by employing a salt-tolerant *Lactobacillus* having a fast enrichment rate with respect to contaminated bacteria having salt tolerance, while controlling contaminated bacteria having no salt tolerance.

According to the culturing method of the present invention, it is possible to sufficiently culture the salt-tolerant *Lactobacillus* according to the present invention even by an open-system culture apparatus (provided that apparatus capable of sterilization and incubation) without using a sealed sterile culture apparatus.

[3] Method of Preparing Salt-Tolerant *Lactobacillus*:

The salt-tolerant *Lactobacillus* of the present invention can be prepared by culturing, followed by a treatment such as sterilization, or the like. Specifically, after completion of the culturing, medium components containing sodium chloride are removed by means such as centrifugation, or the like, followed by washing and purification. Then, heat sterilization is performed, and then drying and concentration are performed by means such as lyophilizing, reduced pressure drying, hot air drying, and the like. As described above, the salt-tolerant *Lactobacillus* of the present invention can be prepared.

In addition, the heat sterilization is not particularly limited, but specifically autoclave sterilization (121° C., 20 minutes) or the same degree of sterilization (105° C., 30 minutes) is preferable.

[4] Immunostimulant:

The immunostimulant of the present invention contains the salt-tolerant *Lactobacillus* of the present invention. Since this immunostimulant contains the salt-tolerant *Lactobacillus* (for example, salt-tolerant *Lactobacillus* derived from miso), safety is high (foodstuff suitability is high), and the immunostimulant is easily produced since the salt-tolerant *Lactobacillus* is used. In addition, by containing the salt-tolerant *Lactobacillus* of the present invention, an immunostimulatory action is exerted.

A content ratio of the immunostimulant of the present invention is not particularly limited as long as the salt-tolerant *Lactobacillus* of the present invention is contained as an active ingredient. In addition, the immunostimulant of the present invention may contain indigestible dextrin, oligosaccharide, dextrin, silicon dioxide, and the like, as other components in addition to the salt-tolerant *Lactobacillus* of the present invention.

Further, the immunostimulant of the present invention may contain a cultured product, a bacterial cell or a bacterial cell component obtained by the method of culturing the salt-tolerant *Lactobacillus* of the present invention.

Further, the immunostimulant of the present invention itself may be used as a food and drink, a supplement, a medicine, or the like, or may be used by being added to foods and drinks, supplements, pharmaceuticals, and the like. There are no particular limitations on food and drink, for example, may include processed seasoning of materials for miso, instant miso soup, cooked miso (processed miso), name-miso such as kinzanji miso, soy sauce, soup, season sauce, seasoning sauce, pickle (lightly-pickled), and the like, seasoning foods of materials for rice, or the like, side dishes, sweet rice drinks (yeast drinks), sweet red-bean porridge, and the like.

EXAMPLES

Hereinafter, the present invention is described specifically based on Examples, but the present invention is not limited to these Examples.

Example 1

(Measurement Test for Viability and Activation Potency of B Cell)

*Tetragenococcus halophilus* bacterial cells (i.e., salt-tolerant lactobacilli) which were sterilized and isolated in the brewing process of miso (i.e., derived from miso) were added to B cells (B220 positive cells) derived from the spleen of experimental mouse (C57BL/6) and the cells were cultured, and viability of spleen B cells and activation potency of spleen B cells were investigated. Hereinafter, "spleen B cell" is sometimes simply referred to as "B cell" in the present Example.

(1) Preparation of *Lactobacillus* Suspension:

56 strains of lactobacilli isolated from the brewing process of miso were cultured at 30° C. for 4 to 7 days using "10SG10N medium", respectively. After that, all of the 56 strains were autoclave-sterilized at 121° C. for 15 minutes to obtain a culture liquid for each strain.

In addition, "10SG10N medium" was obtained by mixing 10 v/v % soy sauce ("koikuchi soy-sauce" made by Ichibiki Co., Ltd.), 1.0 w/v % glucose, 1.0 w/v % yeast extract, 0.5 w/v % polypeptone, 0.2 w/v % sodium acetate trihydrate, 10 w/v % sodium chloride, 0.0025 w/v % "Tween 80 (poly(oxyethylene)sorbitan monooleate)", 0.02 w/v % magnesium sulfate heptahydrate, 0.001 w/v % manganese sulfate tetrahydrate, and 0.001 w/v % iron sulfate heptahydrate, adjusting the pH to 6.8, and autoclaving. In addition, "v/v %" indicates (volume/volume) %.

Next, each culture liquid obtained by sterilization treatment was centrifuged at 5000 rpm for 10 minutes. Thereafter, strains were collected, washed three times with distilled water, suspended in distilled water, and lyophilized to obtain bacterial cells (56 strains). Thereafter, each of the lyophilized bacterial cells was suspended in phosphate buffer (PBS) having a pH of 6.8 to a concentration of 0.1 mg/mL to prepare 56 strains of *Lactobacillus* suspension.

(2) Preparation of B Cells:

Cells collected from the spleen of the experimental mouse (C57BL/6) were collected in a 1.5 mL reaction tube (manufactured by Greiner Bio-One), and 0.5 mL of erythrocyte lysis buffer (0.155 M $NH_4Cl$, 0.01 M Tris-HCl, pH 7.5) was added to suspend the cells. Thereafter, 0.5 mL of phosphate buffer (PBS) at pH 6.8 was added, and the mixture was centrifuged at 1200 rpm for 5 minutes and washed once with a phosphate buffer (PBS) at pH 6.8.

After suspension in the basic medium, biotin-anti-B220 antibody (manufactured by TONBO Biosciences) was added, and the mixture was refrigerated (5° C.) and left to stand for 30 minutes. In addition, the basic medium was supplemented with fetal bovine serum (manufactured by SAFC Biosciences) so as to be 9 (w/v %), wherein the fetal bovine serum was inactivated by heating RPMI 1640 with 0.3 g/L L-glutamic acid added (manufactured by Nacalai Tesque, Inc.), which was added with a penicillin-streptomycin mixed solution (100 U/mL-100 μg/mL in a medium manufactured by Nacalai Tesque, Inc.) and 2-mercaptoethanol (50 μM in a medium manufactured by Nacalai Tesque, Inc.), at 55° C. for 30 minutes.

After standing, the mixture was centrifuged at 1200 rpm for 5 minutes, washed twice with a phosphate buffer solution (PBS) of pH 6.8, and then suspended in a phosphate buffer solution (PBS) of pH 6.8. Thereafter, magnetic beads, Streptavidin Particles Plus•DM (manufactured by Nippon Becton Dickinson Company, Ltd) were added and the mixture was refrigerated (5° C.) and left to stand for 30 minutes.

Thereafter, the mixture was centrifuged at 1200 rpm for 5 minutes, washed once with a phosphate buffer solution (PBS) of pH 6.8, resuspended in a phosphate buffer solution (PBS) of pH 6.8, and transferred to a round tube.

Thereafter, the cells were separated with a BD IMag Cell Separation System (manufactured by Nippon Becton Dickinson Company, Ltd), and the cells attracted to the magnet were collected as a positive fraction. The collected positive fraction was resuspended in the basic medium again as "B cell (B220 positive cell)" to prepare a B cell suspension. In addition, the number of cells in the obtained B cell suspension was counted using a hemocytometer.

(3) Cell Culture:

The B cell suspension was adjusted with the basic medium so as to be $2 \times 10^6$ cells/mL, and 0.5 mL of the adjusted B cell suspension was seeded in a 48-well microplate (manufactured by Falcon Corporation) to obtain $1 \times 10^6$ cells/0.5 mL/well. Thereafter, 5 μL of each *Lactobacillus* suspension (0.1 mg/mL) was added and cultured at 37° C. and 5% $CO_2$ for 2 days. In addition, a *Lactobacillus* suspension was obtained by culturing the B cell suspension after adjustment for 2 days without adding bacterial cells (*Lactobacillus* suspension) under the same condition (37° C., 5% $CO_2$) as the level to which the bacterial cells were added, and determined as a control group.

(4) Measurement of Viability and Activation Potency of B Cells:

After culturing, viability and activation potency of each sample (cell culture liquid) were measured using flow cytometry (MACSQuant Analyzer manufactured by Miltenyi Biotech).

First, the cell culture liquid that was cultured in a 48-well microplate was transferred to a 1.5 mL reaction tube (manufactured by Greiner Bio-One), centrifuged at 1200 rpm for 5 minutes, and cells were collected. Thereafter, the collected cells were suspended in 0.2 mL of phosphate buffer (PBS) at pH 6.8, then 1 μL of violetFluor 450-labeled anti-B220 antibody (manufactured by TONBO Biosciences) and 1 μL of APC-labeled anti-CD86 antibody (manufactured by TONBO Biosciences), were added and the mixture was left to stand for 60 minutes in a refrigerator (5° C.).

After standing, the mixture was centrifuged at 1200 rpm for 5 minutes, and the cells were collected and suspended in 0.5 mL of phosphate buffer (PBS) at pH 6.8. Thereafter, 0.5 μL of Propidium Iodide (PI) nucleus staining liquid (manufactured by Cosmo Bio Co., Ltd.) was added to obtain a sample for measurement. This sample for measurement was subjected to measurement using flow cytometry. In addition, for analysis, FCS data analysis software FlowJo (manufactured by FlowJo, LLC) was used. In addition, Propidium Iodide (PI) nucleus staining liquid was used because this staining liquid is a reagent that does not permeate the cell membrane of living cells and can stain dead cells.

(Viability of B Cell)

In the sample for measurement, the number obtained by subtracting the number of added lactobacilli (the number of bacterial cells in the *Lactobacillus* suspension) from the counted number of cells was taken as the total cell number. In addition, among the samples for measurement, the PI-detected cells (i.e., the cells stained with the PI nucleus staining liquid) were regarded as dead cells, the number thereof was counted, and a difference between the total number of cells and the number of dead cells was taken as the number of living cells. Then, a proportion of living cells in total cells (number of living cells/number of total cells× 100) was calculated. Likewise, the proportion of living cells in total cells in control group (group in which no *Lactobacillus* suspension was added) was calculated. Thereafter, these values were compared, and a value of a ratio when the control group was taken as the standard (100) was calculated to be a value of the viability (cell viability) of the B cell. In addition, the cell viability test was repeated, and a mean value ($X^-$) and a standard error (S.E.) were obtained with respect to the value of viability of B cells. Results thereof are shown in FIG. 1 and Table 1. In addition, in FIGS. 1 to 7 and 9 to 14, "CTL" represents a control group. In the present Example, "mean value ($X^-$)" is a mean value of six tests (n=6).

The viability of B cells was evaluated according to the following criteria. A case where a value calculated from Equation "mean value ($X^-$)–standard error (S.E.)" is more than 100 and less than 110 is "A", a case where the value is 110 or more and less than 130 is "AA", and a case where the value is 130 or more is "AAA". Results thereof are shown in Table 1.

(Activation Potency of B Cell)

Figure 2:
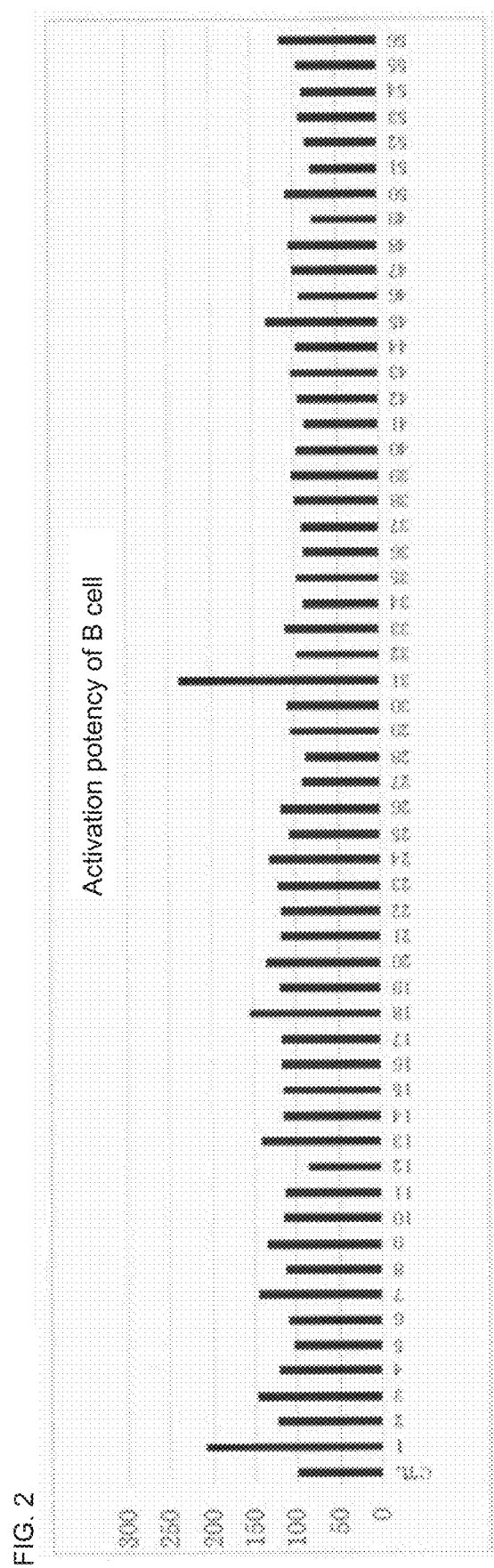
FIG. 2 is a graph showing results of activation potency of the spleen B cells in Example 1.

B cells expressing B220 and CD86 were detected with a violetFluor 450-labeled anti-B220 antibody, which is a cell surface marker of B cells, and an APC-labeled anti-CD86 antibody, which is an activation marker of B cells, and the number of B cells was counted. In addition, a quotient of activated B cells (CD86$^+$, B220$^+$) and non-activated B cells (CD86$^-$, B220$^+$) (a ratio of the number of activated B cells to the number of non-activated B cells) among the B cells (B220 positive cells) was calculated. Similarly, the quotient of activated B cells (CD86$^+$, B220$^+$) and non-activated B cells (CD86$^-$, B220$^+$) in a control group (group in which no *Lactobacillus* suspension was added) was calculated. Thereafter, these values were compared, and a value of a ratio when the control group was taken as the standard (100) was calculated to be a value of the activation potency of the B cell. In addition, the activation potency test of B cells was repeated, and a mean value ($X^-$) and a standard error (S.E.) were obtained with respect to the value of activation potency of B cells. Results thereof are shown in FIG. 2 and Table 1.

The activation potency of B cells was evaluated according to the following criteria. A case where a value calculated from Equation "mean value ($X^-$)–standard error (S.E.)" is more than 100 and less than 110 is "A", a case where the value is 110 or more and less than 130 is "AA", and a case where the value is 130 or more is "AAA". Results thereof are shown in Table 1.

In Tables 1 and 2, "–" in "Evaluation" means that the value calculated by Equation: "mean value ($X^-$)–standard error (S.E.)" is 100 or less. Further, in Table 1, "OK/NG" in "Evaluation" indicates that a case where the value calculated by Equation: "mean value ($X^-$)–standard error (S.E.)" is more than 100 (i.e., a case corresponding to any one of A, AA, and AAA) is "OK" and a case where the value calculated by Equation: "mean value ($X^-$)–standard error (S.E.)" is 100 or less is "NG". Further, in Table 1, "OK/NG" in "Comprehensive Evaluation" indicates that a case where evaluation of the viability and activation potency of B cells is "OK" is set as "OK" and other cases are set as "NG". It may be appreciated that the strain "OK" in the column "Comprehensive Evaluation" has viability of B cell and activation potency of B cell.

"CD86$^+$, B220$^+$" indicates that both CD86 and B220 are expressed on the cell surface. Further, "CD86$^-$, B220$^+$" indicates that CD86 is not expressed and B220 is expressed.

| Strain No. | Viability of B Cell | | | | Activation Potency of B Cell | | | | Comprehensive Evaluation |
|---|---|---|---|---|---|---|---|---|---|
| | Number of Living Cells/Total Number of Cells | | Evaluation | | CD86$^+$, B220$^+$/CD86$^-$, B220$^+$ | | Evaluation | | |
| | $x^-$ | S.E. | — | OK/NG | $x^-$ | S.E. | — | OK/NG | |
| [TABLE 1-1] | | | | | | | | | |
| control | 100 | — | — | — | 100 | — | — | — | — |
| 1 | 192 | 18 | AAA | OK | 207 | 75 | AAA | OK | OK |
| 2 | 133 | 11 | AA | OK | 124 | 24 | — | NG | NG |
| 3 | 129 | 19 | AA | OK | 147 | 34 | AA | OK | OK |
| 4 | 125 | 15 | AA | OK | 121 | 21 | — | NG | NG |
| 5 | 121 | 15 | A | OK | 103 | 20 | — | NG | NG |
| 6 | 116 | 12 | A | OK | 109 | 29 | — | NG | NG |
| 7 | 99 | 16 | — | NG | 145 | 28 | AA | OK | NG |
| 8 | 134 | 13 | AA | OK | 113 | 16 | — | NG | NG |
| 9 | 100 | 9 | — | NG | 134 | 23 | AA | OK | NG |
| 10 | 116 | 18 | — | NG | 116 | 19 | — | NG | NG |
| 11 | 100 | 10 | — | NG | 114 | 26 | — | NG | NG |
| 12 | 106 | 9 | — | NG | 85 | 12 | — | NG | NG |
| 13 | 115 | 9 | A | OK | 140 | 27 | AA | OK | OK |
| 14 | 99 | 11 | — | NG | 116 | 19 | — | NG | NG |
| 15 | 120 | 13 | A | OK | 116 | 9 | A | OK | OK |
| 16 | 115 | 8 | A | OK | 118 | 24 | — | NG | NG |
| 17 | 109 | 9 | — | NG | 117 | 13 | A | OK | NG |
| 18 | 106 | 12 | — | NG | 155 | 41 | AA | OK | NG |
| 19 | 109 | 7 | A | OK | 119 | 14 | A | OK | OK |
| 20 | 90 | 8 | — | NG | 135 | 28 | A | OK | NG |
| 21 | 97 | 5 | — | NG | 118 | 22 | — | NG | NG |
| 22 | 98 | 7 | — | NG | 117 | 17 | — | NG | NG |

-continued

| | | | | | | | | | |
|---|---|---|---|---|---|---|---|---|---|
| 23 | 94 | 6 | — | NG | 122 | 19 | A | OK | NG |
| 24 | 85 | 14 | — | NG | 130 | 21 | — | NG | NG |
| 25 | 104 | 6 | — | NG | 107 | 25 | — | NG | NG |
| 26 | 113 | 14 | — | NG | 117 | 14 | A | OK | NG |
| 27 | 97 | 7 | — | NG | 92 | 21 | — | NG | NG |

[TABLE 1-2]

| | | | | | | | | | |
|---|---|---|---|---|---|---|---|---|---|
| control | 100 | — | — | — | 100 | — | — | — | — |
| 28 | 99 | 9 | — | NG | 88 | 3 | — | NG | NG |
| 29 | 99 | 11 | — | NG | 105 | 29 | — | NG | NG |
| 30 | 146 | 11 | AA | OK | 110 | 6 | A | OK | OK |
| 31 | 109 | 8 | A | OK | 238 | 11 | AAA | OK | OK |
| 32 | 84 | 10 | — | NG | 98 | 8 | — | NG | NG |
| 33 | 87 | 17 | — | NG | 110 | 13 | — | NG | NG |
| 34 | 112 | 23 | — | NG | 90 | 9 | — | NG | NG |
| 35 | 105 | 17 | — | NG | 97 | 11 | — | NG | NG |
| 36 | 110 | 20 | — | NG | 90 | 7 | — | NG | NG |
| 37 | 116 | 29 | — | NG | 91 | 11 | — | NG | NG |
| 38 | 99 | 29 | — | NG | 99 | 3 | — | NG | NG |
| 39 | 93 | 29 | — | NG | 104 | 2 | A | OK | NG |
| 40 | 92 | 15 | — | NG | 98 | 11 | — | NG | NG |
| 41 | 84 | 21 | — | NG | 87 | 6 | — | NG | NG |
| 42 | 94 | 29 | — | NG | 95 | 3 | — | NG | NG |
| 43 | 99 | 16 | — | NG | 104 | 3 | — | NG | NG |
| 44 | 107 | 9 | — | NG | 97 | 7 | — | NG | NG |
| 45 | 76 | 18 | — | NG | 133 | 6 | AA | OK | NG |
| 46 | 93 | 22 | — | NG | 93 | 12 | — | NG | NG |
| 47 | 76 | 13 | — | NG | 101 | 4 | — | NG | NG |
| 48 | 79 | 11 | — | NG | 105 | 16 | — | NG | NG |
| 49 | 103 | 7 | — | NG | 77 | 9 | — | NG | NG |
| 50 | 83 | 10 | — | NG | 110 | 13 | — | NG | NG |
| 51 | 94 | 13 | — | NG | 79 | 8 | — | NG | NG |
| 52 | 79 | 14 | — | NG | 85 | 8 | — | NG | NG |
| 53 | 87 | 25 | — | NG | 94 | 4 | — | NG | NG |
| 54 | 96 | 19 | — | NG | 90 | 15 | — | NG | NG |
| 55 | 97 | 17 | — | NG | 96 | 3 | — | NG | NG |
| 56 | 86 | 16 | — | NG | 115 | 5 | A | OK | NG |

"AAA": Value of Mean Value ($\bar{x}$) - Standard Error (S.E.) is 130 or more.
"AA": Value of Mean Value ($\bar{x}$) - Standard Error (S.E.) is 110 or more and less than 130.
"A": Value of Mean Value ($\bar{x}$) - Standard Error (S.E.) is more than 100 and less than 110.
"—": Value of Mean Value ($\bar{x}$) - Standard Error (S.E.) is 100 or less.

Among 56 strains of lactobacilli isolated from the brewing process of miso, seven strains Nos. 1, 3, 13, 15, 19, 30, and 31 (hereinafter sometimes referred to as "representative strains") had high viability of B cells and high activation potency of B cells (see Table 1). As shown in Table 1, it is considered that these salt-tolerant lactobacilli directly act on B cells to improve the viability and activation potency of B cells. In addition, since these salt-tolerant lactobacilli are derived from miso, foodstuff suitability is high (i.e., safety is high). Further, culturing is simple because the salt-tolerant Lactobacillus can grow at a high salinity concentration in which it is difficult for the contaminated bacteria to be propagated. Therefore, these salt-tolerant lactobacilli are easily produced.

In the present Example, B cells were analyzed focusing on B220 positive cells, but similar results were obtained when analyzing with CD19 positive cells instead of B220 positive cells. From this result, it could be confirmed that the viability and activation potency of B cells were improved by a predetermined strain.

In addition, the strain No. 1 is a salt-tolerant Lactobacillus of Accession number NITE BP-02318, the strain No. 3 is a salt-tolerant Lactobacillus of Accession number NITE BP-02319, the strain No. 13 is a salt-tolerant Lactobacillus of Accession number NITE BP-02320, the strain No. 15 is a salt-tolerant Lactobacillus of Accession number NITE BP-02321, the strain No. 19 is a salt-tolerant Lactobacillus of Accession number NITE BP-02322, the strain No. 30 is a salt-tolerant Lactobacillus of Accession number NITE BP-02323, and the strain No. 31 is a salt-tolerant Lactobacillus of Accession number NITE BP-02324.

Example 2

Strains (No. 1, 3, 13, 15, 19, 30, and 31) in which both the viability and activation potency of B cells are high and other arbitrary strains (No. 2, 20, 26, 28, 34, and 49) were used as test strains, and influence on the total spleen cells (total spleen cells) was examined.

(Measurement Test for Viability and Activation Potency of Cell)

Each test strain was sterilized and the bacterial cells after sterilization were added to the spleen cells of the experimental mouse (C57BL/6) and cultured, and after culturing, viability of the total spleen cells, viability of the spleen B cells and the spleen T cell, and activation potency of spleen B cells and spleen T cells were investigated. Hereinafter, in the present Example, "spleen B cells" may be simply referred to as "B cells", and "spleen T cells" may be simply referred to as "T cells". In addition, in present Example 2, unlike Example 1, B cells were not isolated. In other words, B cells, T cells, dendritic cells, NK cells, and the like were contained in the cells (total spleen cells) used for the test.

(1) Preparation of Lactobacillus Suspension:

The same Lactobacillus suspension prepared in Example 1 was used.

(2) Preparation of Spleen Cell Suspension:

Cells collected from the spleen of the experimental mouse (C57BL/6) were collected in a 1.5 mL reaction tube (manufactured by Greiner Bio-One), and 0.5 mL of erythrocyte lysis buffer (0.155 M $NH_4Cl$, 0.01 M Tris-HCl, pH 7.5) was added to suspend the spleen cells. Thereafter, 0.5 mL of phosphate buffer (PBS) at pH 6.8 was added, and the mixture was centrifuged at 1200 rpm for 5 minutes and washed twice with a phosphate buffer (PBS) at pH 6.8.

The mixture was suspended in a basic medium to prepare a spleen cell suspension. Further, the same basic medium as in Example 1 was used. The number of cells of the obtained spleen cell suspension was calculated using a hemocytometer.

(3) Cell Culture:

The spleen cell suspension was adjusted with the basic medium so as to be $2 \times 10^6$ cells/mL, and 0.5 mL of the adjusted spleen cell suspension was seeded in a 48-well microplate (manufactured by Falcon Corporation) to obtain $1 \times 10^6$ cells/0.5 mL/well. Thereafter, 5 µL of each *Lactobacillus* suspension (0.1 mg/mL) was added and cultured at 37° C. and 5% $CO_2$ for 2 days. In addition, a *Lactobacillus* suspension was obtained by culturing the spleen cell suspension after adjustment for 2 days without adding bacterial cells (*Lactobacillus* suspension) under the same condition (37° C., 5% $CO_2$) as the level to which the cells were added, and determined as a control group.

(4) Measurement of Viability and Activation Potency of Cells:

After culturing, viability and activation potency of each sample (cell culture liquid) were measured using flow cytometry (MACSQuant Analyzer manufactured by Miltenyi Biotech).

First, the cell culture liquid that was cultured in a 48-well microplate was transferred to a 1.5 mL reaction tube (manufactured by Greiner Bio-One), centrifuged at 1200 rpm for 5 minutes, and cells were collected. Thereafter, the collected cells were suspended in 0.2 mL of phosphate buffer solution (PBS) at pH 6.8, 1 µL of each of the following four antibodies was added, and each mixture was left to stand for 60 minutes in refrigerator (5° C.).

The added four antibodies included violetFluor 450-labeled anti-B220 antibody (manufactured by TONBO Biosciences), APC-labeled anti-CD86 antibody (manufactured by TONBO Biosciences), Brilliant Violet 510-labeled anti-CD4 antibody (manufactured by BioLegend, Inc), and PE-labeled anti-CD69 antibody (manufactured by BioLegend, Inc).

After standing, the mixture was centrifuged at 1200 rpm for 5 minutes, and the cells were collected and suspended in 0.5 mL of phosphate buffer (PBS) at pH 6.8. Thereafter, 0.5 µL of Propidium Iodide (PI) nucleus staining liquid (produced by Cosmo Bio Inc.) was added to obtain a sample for measurement. This sample for measurement was subjected to measurement using flow cytometry. In addition, for analysis, FCS data analysis software FlowJo (manufactured by FlowJo, LLC) was used.

(Viability of Cell)

Figure 3:
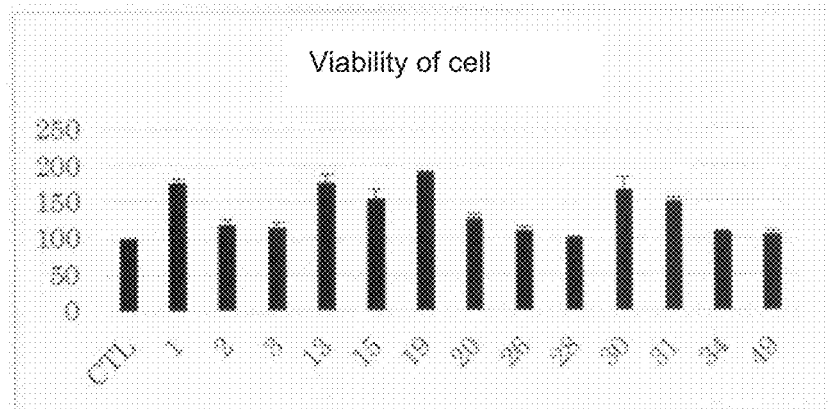
FIG. 3 is a graph showing results of viability of total spleen cells in Example 2.

In the sample for measurement, the number obtained by subtracting the number of added lactobacilli (the number of bacterial cells in the *Lactobacillus* suspension) from the counted number of cells was taken as the total cell number. In addition, among the samples for measurement, the PI-detected cells (i.e., the cells stained with the PI nucleus staining liquid) were regarded as dead cells, the number thereof was counted, and a difference between the total number of cells and the number of dead cells was taken as the number of living cells. Then, a proportion of living cells in total cells (number of living cells/number of total cells × 100) was calculated. Likewise, the proportion of living cells in total cells in a control group (group in which no *Lactobacillus* suspension was added) was calculated. Thereafter, these values were compared, and a value of a ratio when the control group was taken as the standard (100) was calculated to be a value of the viability (cell viability) of the cell. In addition, the cell viability test was repeated, and a mean value ($X^-$) and a standard error (S.E.) were obtained with respect to the value of viability of cells. Results thereof are shown in FIG. 3 and Table 2. In the present Example, "mean value ($X^-$)" is a mean value of eight tests (n=8).

The viability of cells was evaluated according to the following criteria. A case where a value calculated from Equation "mean value ($X^-$)–standard error (S.E.)" is more than 100 and less than 120 is "A", a case where the value is 120 or more and less than 150 is "AA", and a case where the value is 150 or more is "AAA". Results thereof are shown in Table 2.

(Viability of B Cell)

Figure 4:
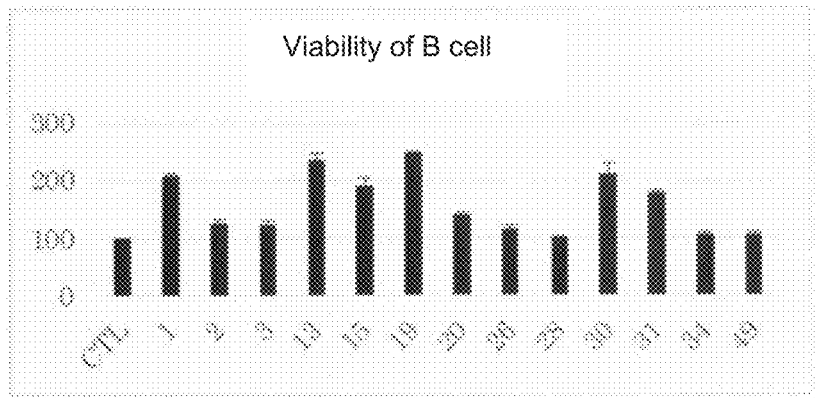
FIG. 4 is a graph showing results of viability of the spleen B cells in Example 2.

B cells were detected with a violetFluor 450-labeled anti-B220 antibody (manufactured by TONBO Biosciences) which is a cell surface marker of B cell. The quotient of the number of B cells among living cells and the number of total cells (the ratio of the number of viable B cells to the total number of cells) was calculated. Further, in the present Example, in the sample for measurement, the number obtained by subtracting the number of added lactobacilli (the number of bacterial cells in the *Lactobacillus* suspension) from the counted number of cells was taken as "the total cell number". In addition, among the samples for measurement, the PI-detected cells (i.e., the cells stained with the PI nucleus staining liquid) were regarded as dead cells, the number thereof was counted, and a difference between the total number of cells and the number of dead cells was taken as "the number of living cells". In addition, the proportion of living cells in total cells in control group (group in which no *Lactobacillus* suspension was added) was calculated. Thereafter, these values were compared, and a value of a ratio when the control group was taken as the standard (100) was calculated to be a value of the viability of the B cell. In addition, the viability test of B cells was repeated, and a mean value ($X^-$) and a standard error (S.E.) were obtained with respect to the value of viability of B cells. Results thereof are shown in FIG. 4 and Table 2.

The viability of B cells was evaluated according to the following criteria. A case where a value calculated from Equation "mean value ($X^-$)–standard error (S.E.)" is more than 100 and less than 120 is "A", a case where the value is 120 or more and less than 150 is "AA", and a case where the value is 150 or more is "AAA". Results thereof are shown in Table 2.

(Viability of T Cell)

Figure 5:
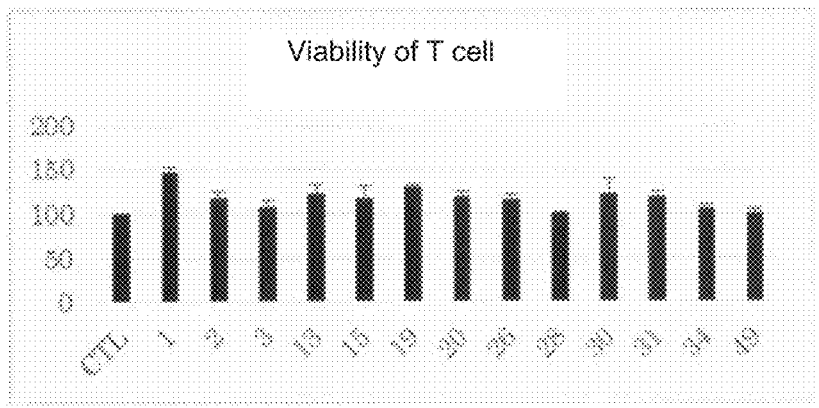
FIG. 5 is a graph showing results of viability of the spleen T cells in Example 2.

T cells were detected with a Brilliant Violet 510-labeled anti-CD4 antibody (BioLegend, Inc) which is a cell surface marker of T cells. The quotient of the number of T cells among living cells and the number of total cells (the ratio of the number of viable T cells to the total number of cells) was calculated. In addition, the proportion of living cells in total cells in a control group (group in which no *Lactobacillus* suspension was added) was calculated. Thereafter, these values were compared, and a value of a ratio when the control group was taken as the standard (100) was calculated to be a value of the viability of the T cell. In addition, the viability test of T cells was repeated, and a mean value ($X^-$)

and a standard error (S.E.) were obtained with respect to the value of viability of T cells. Results thereof are shown in FIG. 5 and Table 2.

The viability of T cells was evaluated according to the following criteria. A case where a value calculated from Equation "mean value ($X^-$)–standard error (S.E.)" is more than 100 and less than 120 is "A", a case where the value is 120 or more and less than 150 is "AA", and a case where the value is 150 or more is "AAA". Results thereof are shown in Table 2.

(Activation Potency of B Cell)

Figure 6:
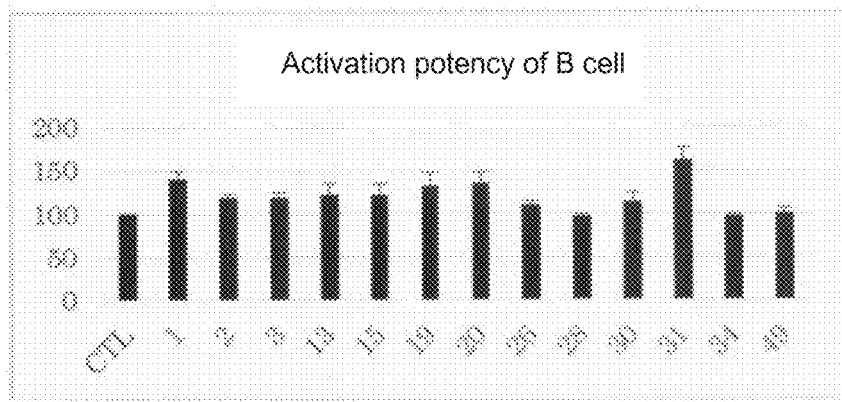
FIG. 6 is a graph showing results of activation potency of the spleen B cells in Example 2.

B cells expressing B220 and CD86 were detected with a violetFluor 450-labeled anti-B220 antibody, which is a cell surface marker of B cells, and an APC-labeled anti-CD86 antibody, which is an activation marker of B cells, and the number of B cells was counted. In addition, a quotient of activated B cells (CD86$^+$, B220$^+$) and non-activated B cells (CD86$^-$, B220$^+$) (a ratio of the number of activated B cells to the number of non-activated B cells) among the B cells (B220 positive cells) was calculated. Similarly, the quotient of activated B cells (CD86$^+$, B220$^+$) and non-activated B cells (CD86$^-$, B220$^+$) in a control group (group in which no *Lactobacillus* suspension was added) was calculated. Thereafter, these values were compared, and a value of a ratio when the control group was taken as the standard (100) was calculated to be a value of the activation potency of the B cell. In addition, the activation potency test of B cells was repeated, and a mean value ($X^-$) and a standard error (S.E.) were obtained with respect to the value of activation potency of B cells. Results thereof are shown in FIG. 6 and Table 2.

The activation potency of B cells was evaluated according to the following criteria. A case where a value calculated from Equation "mean value ($X^-$)–standard error (S.E.)" is more than 100 and less than 120 is "A", a case where the value is 120 or more and less than 150 is "AA", and a case where the value is 150 or more is "AAA". Results thereof are shown in Table 2.

(Activation Potency of T Cell)

Figure 7:
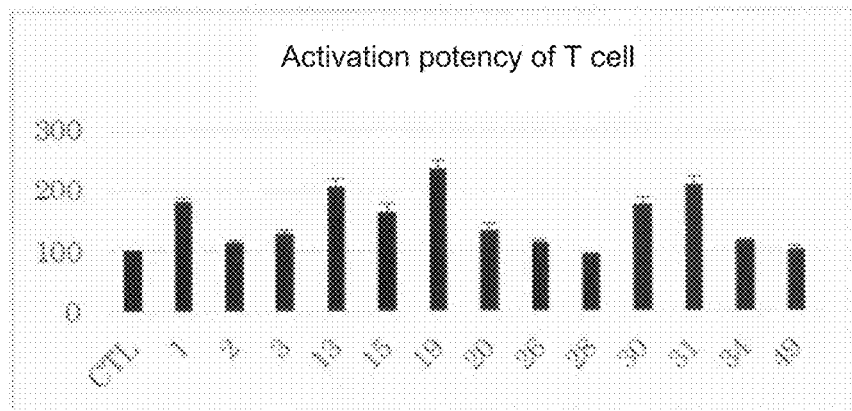
FIG. 7 is a graph showing results of activation potency of the spleen T cells in Example 2.

Cells expressing CD4 and CD69 were detected with a Brilliant Violet 510-labeled anti-CD4 antibody (manufactured by BioLegend, Inc) which is a cell surface marker of T cells and a PE-labeled anti-CD69 antibody (manufactured by BioLegend, Inc) which is an activation marker of T cells, and the number of cells were counted. In addition, a quotient of activated T cells (CD69$^+$, CD4$^+$) and non-activated T cells (CD69$^-$, CD4$^+$) (a ratio of the number of activated T cells to the number of non-activated T cells) among the T cells (CD4 positive (CD4$^+$) cells) was calculated. Similarly, the quotient of activated T cells (CD69$^+$, CD4$^+$) and non-activated T cells (CD69$^-$, CD4$^+$) in a control group (group in which no *Lactobacillus* suspension was added) was calculated. Thereafter, these values were compared, and a value of a ratio when the control group was taken as the standard (100) was calculated to be a value of activation potency of the T cell. In addition, the activation potency test of T cells was repeated, and a mean value ($X^-$) and a standard error (S.E.) were obtained with respect to the value of activation potency of T cells. Results thereof are shown in FIG. 7 and Table 2.

The activation potency of T cells was evaluated according to the following criteria. A case where a value calculated from Equation "mean value ($X^-$)–standard error (S.E.)" is more than 100 and less than 120 is "A", a case where the value is 120 or more and less than 150 is "AA", and a case where the value is 150 or more is "AAA". Results thereof are shown in Table 2.

As shown in Table 2, representative strains (Nos. 1, 3, 13, 15, 19, 30, and 31) had high viability and activation potency of B cells and also high viability and activation potency of T cells similar to in the spleen cells. In other words, it is considered that these salt-tolerant lactobacilli increase the viability and activation potency of B cells and also increase the viability and activation potency of T cells by directly acting on B cells. Therefore, it is considered that these representative strains can be adopted as active ingredients of immunostimulants that exert immunostimulatory action.

Further, more specifically, as clearly shown from Table 2, the salt-tolerant lactobacilli of strains Nos. 1, 13, 19, and 30 had "AAA" in both evaluation of cell viability and evaluation of viability of B cell, and had "A" or more in evaluation of viability of T cell. From these results, it could be appreciated that the viability of each cell (including B cells and T cells) was generally excellent. In addition, it could be appreciated that the salt-tolerant lactobacilli of strains Nos. 1 and 31 had very high viability and activation potency of B cells (evaluation of the viability of B cell was "AAA" and evaluation of the activation potency of B cells was "AA"). In particular, in the salt-tolerant *Lactobacillus* of strain No. 31, the mean value ($X^-$) in the activation potency of B cells was higher than that of the other strains, and the activation potency of B cells was very high.

TABLE 2

| | Cell Viability | | | Viability of B Cell | | |
|---|---|---|---|---|---|---|
| | Number of Living Cells/Total Number of Cells | | Evaluation | Number of B220$^+$ living cells/Total Number of Cells | | Evaluation |
| Strain No. | $x^-$ | S.E. | — | $x^-$ | S.E. | — |
| Control | 100 | — | — | 100 | — | — |
| 1 | 176 | 5 | AAA | 207 | 13 | AAA |
| 2 | 118 | 7 | AA | 126 | 10 | A |
| 3 | 114 | 8 | A | 123 | 10 | A |
| 13 | 175 | 13 | AAA | 235 | 19 | AAA |
| 15 | 152 | 15 | AA | 189 | 24 | AAA |
| 19 | 189 | 3 | AAA | 248 | 11 | AAA |
| 20 | 126 | 7 | A | 139 | 9 | AA |
| 26 | 109 | 7 | A | 117 | 6 | A |
| 28 | 98 | 2 | — | 100 | 4 | — |
| 30 | 165 | 19 | AAA | 211 | 29 | AAA |
| 31 | 148 | 6 | AA | 177 | 7 | AAA |
| 34 | 106 | 4 | A | 106 | 7 | A |
| 49 | 104 | 5 | — | 105 | 9 | — |

TABLE 2-continued

| | Viability of T Cell | | | Activation Potency of B Cell | | |
|---|---|---|---|---|---|---|
| | Number of CD4⁺ Living Cells/Total Number of Cells | | Evaluation | CD86⁺, B220⁺/ CD86⁻, B220⁺ | | Evaluation |
| Strain No. | x⁻ | S.E. | — | x⁻ | S.E. | — |
| Control | 100 | — | — | 100 | — | — |
| 1 | 148 | 8 | AA | 141 | 9 | AA |
| 2 | 117 | 9 | A | 119 | 5 | A |
| 3 | 107 | 5 | A | 119 | 6 | A |
| 13 | 121 | 5 | A | 122 | 14 | A |
| 15 | 117 | 6 | A | 121 | 15 | A |
| 19 | 130 | 8 | AA | 132 | 17 | A |
| 20 | 119 | 7 | A | 136 | 14 | AA |
| 26 | 115 | 11 | A | 110 | 6 | A |
| 28 | 100 | 2 | — | 97 | 3 | — |
| 30 | 122 | 8 | A | 113 | 12 | A |
| 31 | 119 | 6 | A | 161 | 15 | AA |
| 34 | 106 | 3 | A | 96 | 4 | — |
| 49 | 100 | 2 | — | 101 | 5 | — |

| | Activation Potency of T Cell | | |
|---|---|---|---|
| | CD4⁺, CD69⁺/ CD4⁺, CD69⁻ | | Evaluation |
| Strain No. | x⁻ | S.E. | — |
| Control | 100 | — | — |
| 1 | 180 | 10 | AAA |
| 2 | 113 | 11 | A |
| 3 | 129 | 8 | AA |
| 13 | 206 | 14 | AAA |
| 15 | 163 | 18 | AA |
| 19 | 235 | 11 | AAA |
| 20 | 133 | 14 | A |
| 26 | 113 | 13 | A |
| 28 | 93 | 6 | — |
| 30 | 175 | 13 | AAA |
| 31 | 207 | 7 | AAA |
| 34 | 115 | 8 | A |
| 49 | 102 | 9 | — |

"AAA": Value of Mean Value (x⁻) - Standard Error (S.E.) is 150 or more.
"AA": Value of Mean Value (x⁻) - Standard Error (S.E.) is 120 or more and less than 150.
"A": Value of Mean Value (x⁻) - Standard Error (S.E.) is more than 100 and less than 120.
"—": Value of Mean Value (x⁻) - Standard Error (S.E.) is 100 or less.

In Table 2, "B220⁺ viable cell count/total cell count" indicates a ratio of "the number of B cells reacted with violetFluor450-labeled anti-B220 antibody in which PI was not detected" to the total number of cells. The "CD4⁺ viable cell count/total cell count" indicates a ratio of "the number of T cells reacted with Brilliant Violet510-labeled anti-CD4 antibody in which PI was not detected (manufactured by BioLegend, Inc)" to the total number of cells. "CD86⁺, B220⁺/CD86⁻, B220⁺" indicates a value of a ratio of activated B cells (CD86⁺, B220⁺)/non-activated B cells (CD86⁻, B220⁺). "CD4⁺, CD69⁺/CD4⁺, CD69⁻" indicates a value of a ratio of activated T cells/non-activated T cells.

In addition, in the present Example, B cells were analyzed focusing on B220 positive cells, but similar results could be obtained even when analyzing with CD19 positive cells instead of B220 positive cells. From this result, it could be confirmed that the viability and activation potency of B cells were improved by a predetermined strain.

Example 3

Among representative strains, the strain No. 1 and other strains (Nos. 2 and 20) were subjected to microarray analysis to examine gene expression status.

(Investigation of Gene Expression Pattern by DNA Microarray Analysis)
(1) Preparation of RNA:
Cells collected from the spleen of experimental mice (C57BL/6) were inoculated into 6 well microplates (manufactured by Falcon Corporation) so as to be $5 \times 10^6$ cells/5 mL/well in a basic medium. Thereafter, 50 μL of each *Lactobacillus* suspension (0.1 mg/mL) was added and cultured at 37° C. and 5% $CO_2$ for 24 hours. In addition, a *Lactobacillus* suspension was obtained by culturing the spleen cell suspension without adding bacterial cells (*Lactobacillus* suspension) under the same condition (37° C., 5% $CO_2$) as the level to which the bacterial cells were added, and determined as a control group.

The cultured cells were reacted with Biotin-anti-B220 antibody (manufactured by TONBO Biosciences) and Streptavidin Particles Plus DM which are magnetic beads (manufactured by Nippon Becton Dickinson Company, Ltd), and separated with BD IMag Cell Separation System (manufactured by Nippon Becton Dickinson Company, Ltd). The cells (positive fractions) attracted to the magnet were collected as "B cells (B220-positive cells)".

In addition, the spleen cells were produced in the same manner as in Example 2, preparation of *Lactobacillus* suspension and collection of B cells were performed in the same manner as in Example 1.

Total RNA was extracted from B cells isolated from cultured spleen cells using ISOGEN II (manufactured by Nippon Gene Co., Ltd.) for RNA extraction. Then, labeled cDNA was prepared using the extracted total RNA as a template and subjected to DNA microarray analysis.

For DNA microarray analysis, "SurePrint G3 Mouse Gene Expression 8×60 K" manufactured by Agilent Co., Ltd. was used. After that, DNA was analyzed by gene expression software "R version 2.15.1 (The R Foundation)".

"Gene expression amount when adding *Lactobacillus* suspension" with respect to "gene expression amount in a control group" was calculated. Results thereof are shown in Table 3 below. In addition, in Table 3, when the gene expression amount is "2.0" or more, there is a significant difference from the control group.

TABLE 3

| Gene Name | No.1 | No.2 | No.20 |
| --- | --- | --- | --- |
| CD86 | 2.0 | 1.1 | 1.4 |
| CD70 | 3.2 | 1.2 | 1.9 |
| Interleukin-10 | 2.2 | 1.2 | 1.6 |
| Interleukin-12a | 1.3 | 1.1 | 1.0 |
| Interleukin-12b | 1.3 | −1.2 | 1.6 |
| Interleukin-22 | 10.0 | 1.0 | 3.1 |
| Interferon-β | — | — | — |
| Interferon-γ | 8.3 | 1.2 | 3.2 |

*1: Gene expression amount of B cells (relative ratio when expression amount in control group (without addition of *lactobacillus*) is 1).
*2: "—" indicates that detection is impossible.

As a result of DNA microarray analysis, it could be confirmed that expression of CD86 gene and CD70 gene was increased by adding the strain No. 1 to the B cell. The expression of these genes increased, indicating that B cells were activated. Further, it is known that CD86 or CD70 induces ancillary signals via CD28 and CD27 on T cells, respectively, and is important for activation of T cells. It is considered that the activation of T cells is also affected by adding the strain No. 1.

From the result of DNA microarray analysis, it could be appreciated that the strain No. 1 activated both B cells and T cells (i.e., the viability and activation potency of B cells were improved, and the viability and activation potency of T cells were also improved) even in gene levels.

In addition, it could be appreciated that by adding the salt-tolerant *Lactobacillus* of the present invention, the expression amount of interferon-γ increased, and an immunostimulatory action by inducing the production of interferon-γ was also obtained. It is known that interferon-γ is a cytokine having an antiviral effect.

In addition, the expression amount of interleukin-10 also increased by adding the salt-tolerant *Lactobacillus* of the present invention. Interleukin-10 is a potent anti-inflammatory cytokine and suppresses the release of inflammatory cytokines in various cells. Therefore, according to the salt-tolerant *Lactobacillus* of the present invention, it is thought that the salt-tolerant *Lactobacillus* acts not only on the immunostimulatory effect but also on immune tolerance to achieve maturation of an immune function.

In addition, the expression amount of interleukin-22 also increased by adding the salt-tolerant *Lactobacillus* of the present invention. Interleukin-22 is involved in tissue repair, cell survival and proliferation, and mucosal barrier defense.

In addition, it could be appreciated that the strain No. 1 did not directly affect the expression of interleukin-12 and interferon-β via B cells. Interleukin-12 is a cytokine that is characterized by an activating action on killer T cells or NK cells (natural killer cells). Interferon-β is a physiologically active material that is first produced by immune cells to exert antiviral functions.

It is presumed that the gene expression pattern obtained by adding the strain No. 1 of the present invention is not known in the related art, and an immunostimulatory action is shown as an unknown action mechanism.

In addition, it is known that interleukin-22 is produced from immune cells such as CD4-positive T cells, NK cells, NKT cells and the like, but production from B cells is not known, and there is no report on *Lactobacillus* increasing the expression amount of interleukin-22 based on B cells.

Comparative Example 1

(Examination of Salinity Concentration of Medium)

With respect to representative salt-tolerant *Lactobacillus* used in soy sauce brewing (*Tetragenococcus halophilus* DA-297 strain), six samples were prepared according to six steps of salinity concentrations of medium, and culture rates at each step were compared. In addition, co-culture was performed by adding the salt-tolerant *Lactobacillus* (*Tetragenococcus halophilus* DA-297 strain) while adding bacteria simultaneously, and culture rates thereof were compared.

Salt-tolerant *Staphylococcus* bacteria were used as bacteria. In addition, general bacteria (germs) including food poisoning bacteria are not resistant to sodium chloride, and when the salinity is higher than 8 w/v %, proliferation thereof can be suppressed sufficiently, but some of *Staphylococcus* bacteria is known to be salt-tolerant. Therefore, the *Staphylococcus* bacteria can be determined as one of microorganisms having the greatest pollution risk in the culturing of *Tetragenococcus halophilus*.

In addition, the used *Staphylococcus* strain is a strain which is incorporated into the medium at 35° C. in a step of culturing the soysauce *Lactobacillus* in a soy sauce manufacturing process, and is the most salt-tolerant strain (SN-2820 strain) among the strains. In addition, to the medium, 20 w/v % soysauce ("koikuchi soy-sauce" made by Ichibiki Co., Ltd.), 1.7 w/v % glucose, and sodium chloride were added to have a salinity concentration of 14 w/v %, and the pH was adjusted to pH 6.8. This strain could proliferate slightly even in the medium with the highest concentration of sodium chloride (salinity concentration 18 w/v %).

Further, the sequence listing shows the partial nucleotide sequence of 16SrDNA of salt-tolerant *Staphylococcus* bacterium SN-2820 strain. The nucleotide sequences shown in the sequence listing were searched for nucleotide sequences having high homology in the existing nucleotide sequence databases, and as a result, the nucleotide sequences were identical to 16SrDNA partial nucleotide sequences of *Staphylococcus saprophyticus* subsp. *saprophyticus*. From these results, the SN-2820 strain was classified into *Staphylococcus saprophyticus* subsp. *saprophyticus*.

(Medium)

Koikuchi soy-sauce (made by Ichibiki Co., Ltd.) as nitrogen source and trace minerals, glucose (made by Kato Kagaku Co., Ltd.) as a carbon source were used, and sodium chloride (made by Kato Kagaku Co., Ltd.) and water were used as other raw materials. As described above, a medium which is simple and contains only food ingredients was reviewed.

The Koikuchi soy-sauce had a concentration of 20 v/v % for all samples, and the glucose had a concentration of 1.7 w/v % for all samples. Further, an addition amount of sodium chloride was adjusted so that the salinity concentration of the medium was divided into 6 steps such as 8, 10, 12, 14, 16, and 18 w/v %. In addition, all samples were adjusted with sodium hydroxide (made by Kato Kagaku Co., Ltd.), which is a food additive, so that the pH was 7.0.

The medium in an amount of 10 mL was put into a test tube (diameter 18 mm×180 mm), the tube was capped with Silicosen® (manufactured by Shin-Etsu Polymer Co., Ltd.) and sterilized with an autoclave at 121° C. for 15 minutes.

(Culturing)

On the assumption of subculture, 1 v/v % of *Tetragenococcus halophilus* DA-297 strain that was pre-cultured in the same medium was added and the cells were inoculated so that the number of initial bacteria was $1.5 \times 10^7$ cfu/mL. In addition, the *Staphylococcus* bacterium SN-2820 strain, which was pre-cultured, was added assuming that 0.1 v/v % of *Staphylococcus* bacteria were added to the *Tetragenococcus halophilus* DA-297 strain. Here, the number of initial *Staphylococcus* bacteria was $1.1 \times 10^4$ cfu/mL. Thereafter, *Tetragenococcus halophilus* DA-297 strain was stationary cultured for 24 hours and 72 hours in a thermostat at 30° C.

(Measurement of the Number of Bacteria)

The viable cell count of the *Tetragenococcus halophilus* DA-297 strain after stationary culture for 24 hours was determined by applying a dilute bacterial liquid to the "10SG10N plate medium", culturing the liquid (anaerobic culture at 30° C. for 4 days), and counting the number of colonies. In addition, the *Staphylococcus* bacteria were cultured by a standard agar medium (SA) plate culture method, and then the number of bacteria cells (living cells) was measured.

"10SG10N plate medium" was prepared by containing 10 v/v % soy sauce ("Koikuchi soy-sauce" made by Ichibiki Co., Ltd.), 1.0 w/v % glucose, 1.0 w/v % yeast extract, 0.5 w/v % polypeptone, 0.2 w/v % sodium acetate trihydrate, 10 w/v % sodium chloride, 0.0025 w/v % Tween 80, 0.02 w/v % magnesium sulfate heptahydrate, 0.001 w/v % manganese sulfate tetrahydrate, 0.001 w/v % of iron sulfate heptahydrate, and satisfying pH at 6.8, and agar 2%.

In addition, the value obtained by dividing the number of bacteria (living cells) after 24 hours by the number of initial bacteria (number of bacteria after 24 hours/number of initial bacteria) was calculated as a proliferation factor (times/24 hours) of 24 hours. Results thereof are shown in Table 4 below.

Further, the number of bacteria (the total amount (final yield) of living cells and dead cells) was determined using a hemocytometer under a microscope, wherein the number of bacteria of *Tetragenococcus halophilus* DA-297 after 72 hours was determined as the "total number of bacteria".

TABLE 4

| | Salinity Concentration (w/v%) of Medium | 18 | 16 | 14 | 12 | 10 | 8 |
|---|---|---|---|---|---|---|---|
| Initial | Number of Tetragenococcus Halophilus DA-297 Strains (cfu/mL) | 1.5E+07 | 1.5E+07 | 1.5E+07 | 1.5E+07 | 1.5E+07 | 1.5E+07 |
| | Number of Salt-tolerant Staphylococcus Bacteria SN-2820 Strains (cfu/mL) | 1.1E+04 | 1.1E+04 | 1.1E+04 | 1.1E+04 | 1.1E+04 | 1.1E+04 |
| After 24 hrs | Number of Tetragenococcus Halophilus DA-297 Strains (cfu/mL) | 1.9E+08 | 4.5E+08 | 8.5E+08 | 8.5E+08 | 1.2E+09 | 1.1E+09 |
| | Number of Salt-tolerant Staphylococcus Bacteria SN-2820 Strains (cfu/mL) | 3.1E+04 | 9.6E+04 | 1.2E+05 | 4.3E+05 | 3.0E+06 | 6.2E+06 |
| | pH of Medium | 6.45 | 6.10 | 5.56 | 5.05 | 5.12 | 5.21 |
| | Proliferation Factor of Tetragenococcus Halophilus DA-297 Strains (times/24 hrs) | 13 | 30 | 57 | 57 | 78 | 72 |
| | Proliferation Factor of Salt-tolerant Staphylococcus Bacteria SN-2820 Strains (times/24 hrs) | 3 | 9 | 12 | 41 | 282 | 582 |
| Final Yield (After 72 hrs) | Number of Tetragenococcus Halophilus DA-297 Strains (cfu/mL) | 1.0E+09 | 2.0E+09 | 3.5E+09 | 5.0E+09 | 5.2E+09 | 5.5E+09 |

As shown in Table 4, it could be appreciated that *Tetragenococcus halophilus* DA-297 strain was able to proliferate vigorously at a salinity concentration of 8 to 14 w/v % and to sufficiently proliferate even at 18 w/v %. Meanwhile, the bacteria of the *Staphylococcus* proliferated well in the range of the salinity concentration of 8 to 18 w/v % as the salinity concentration was lower. In addition, at the salinity concentration of 10 w/v % or less, the proliferation factor was higher than that of *Tetragenococcus halophilus* DA-297 strain, and at the salinity concentration of 8 w/v %, the strains were enriched at a rate of about 8 times as compared to *Tetragenococcus halophilus* DA-297 strain.

From the above results, it was found that it is preferable to set the salinity concentration of the culture medium to 14 w/v % or more in the case of *Tetragenococcus halophilus* DA-297 strain. Meanwhile, the final yield of the salt-tolerant *Lactobacillus* is lowered as the salinity concentration is higher. Therefore, salt-tolerant *Lactobacillus* derived from miso that had a higher growth rate than that of the salt-tolerant *Staphylococcus* bacteria even at a salt content of 12 w/v % was examined in Example 4 below.

Example 4

(Selection of Salt-Tolerant *Lactobacillus*)

In the present embodiment, when the salinity concentration of the medium was 12 w/v %, seven strains (7 samples) of Nos. 1, 3, 13, 15, 19, 30 and 31 were screened for salt-tolerant *Lactobacillus* with a higher enrichment rate than that of salt-tolerant *Staphylococcus* bacterium SN-2820 strain.

(Medium)

Koikuchi soy-sauce (made by Ichibiki Co., Ltd.) as nitrogen source and trace minerals, glucose (made by Kato Kagaku Co., Ltd.) as a carbon source were used, and sodium chloride (made by Kato Kagaku Co., Ltd.) and water were used as other raw materials. As described above, a medium which is simple and contains only food ingredients was reviewed.

Specifically, the medium was prepared by mixing 20 v/v % Koikuchi soy-sauce (made by Ichibiki Co., Ltd.) 1.7 w/v % glucose, and sodium chloride with water so that the salinity concentration was 12 w/v %, and then adjusting pH to 7.0 with sodium hydroxide (made by Kato Kagaku Co., Ltd.) as a food additive.

Into a test tube (diameter 18 mm×180 mm), 10 mL of the prepared medium was put, and the test tube was capped with Silicosen® and sterilized with an autoclave at 121° C. for 15 minutes.

(Culturing)

On the assumption of subculture, 1 v/v % of each salt-tolerant *Lactobacillus* that was pre-cultured in the same medium was added. Here, the number of initial bacteria was $3.7 \times 10^6$ to $1.5 \times 10^7$ cfu/mL. In addition, the *Staphylococcus* bacterium SN-2820 strain, which was pre-cultured, was added assuming that 1 v/v % of *Staphylococcus* bacteria were added to the salt-tolerant *Lactobacillus*. The number of initial *Staphylococcus* bacteria was $1.8 \times 10^5$ to $5.7 \times 10^5$ cfu/mL. Then, all the samples (seven strains and the salt-tolerant *Staphylococcus* bacteria SN-2820 strains) were subjected to stationary culture for 20 hours in a thermostat at 30° C.

(Measurement of the Number of Bacteria)

Then, the measurement of the number of bacteria was performed. The measurement of the number of bacteria was performed in the same manner as in Comparative Example 1.

The value obtained by dividing the number of bacteria after 20 hours by the number of initial bacteria (number of bacteria after 20 hours/number of initial bacteria) was calculated as a proliferation factor (times/20 hours) of 20 hours. Results thereof are shown in Table 5 below.

tends to be slow as compared with the case of other salinity concentrations. Therefore, the salt-tolerant *Lactobacillus* of the present invention is preferably cultured at a salinity concentration of 11 to 16 w/v %, more preferably at a salinity concentration of 12 to 16 w/v %, and most preferably, a salinity concentration of 12 to 14 w/v %.

In addition, the amount of histamine was measured for a supernatant of the pre-culture liquid used in this experiment. For the measurement, "check color histamine (manufactured by Kikkoman Biochemifa Company)" was used. As a result of the measurement, it could be appreciated all *Lactobacillus* culture liquids had the histamine concentration less than 20 ppm, and there was no histamine producing ability. Further, the measurement method was performed in accordance with the instruction manual attached to "Check color histamine".

Example 5

(Measurement Test of Cytokine-Producing Cells)

The test cells after the sterilization treatment were added to the spleen cells of the experimental mice (C57BL/6) and co-cultured to measure the proportion of cells producing various cytokines of interleukin-22, interleukin-10, and interferon-γ. Representative strains (Nos. 1, 3, 13, 15, 19, 30, and 31) and other arbitrary strains (Nos. 2 and 20) were used as test strains.

(1) Preparation of *Lactobacillus* Suspension:

A *Lactobacillus* suspension was prepared in the same manner as in Example 1 except that the suspension was suspended to a concentration of 1 mg/mL in phosphate buffer (PBS) of pH 6.8.

TABLE 5

| | Strain Name | No. 1 | No. 3 | No. 13 | No. 15 | No. 19 | No. 30 | No. 31 |
|---|---|---|---|---|---|---|---|---|
| Initial | Number of Salt-tolerant Lactobacilli Strains (cfu/mL) | 1.0E+07 | 3.7E+06 | 2.9E+06 | 4.9E+06 | 1.5E+07 | 7.6E+06 | 5.6E+06 |
| | Number of Salt-tolerant Staphylococcus Bacteria SN-2820 Strains (cfu/mL) | 1.8E+05 | 2.7E+05 | 5.7E+05 | 4.6E+05 | 2.6E+05 | 2.9E+05 | 1.2E+05 |
| After 20 hrs | Number of Salt-tolerant Lactobacilli Strains (cfu/mL) | 3.5E+08 | 6.8E+08 | 7.9E+07 | 2.0E+08 | 6.1E+07 | 2.0E+08 | 3.9E+08 |
| | Number of Salt-tolerant Staphylococcus Bacteria SN-2820 Strains (cfu/mL) | 1.8E+06 | 3.3E+06 | 1.1E+06 | 1.2E+06 | 3.8E+06 | 2.6E+06 | 1.2E+06 |
| | Proliferation Factor of Salt-tolerant Lactobacilli (times/20 hrs) | 34 | 184 | 27 | 41 | 4 | 26 | 70 |
| | Proliferation Factor of Salt-tolerant Staphylococcus Bacteria SN-2820 Strains (times/20 hrs) | 10 | 12 | 2 | 3 | 15 | 9 | 10 |

As shown in Table 5, it could be appreciated that strains (No. 1, No. 3, No. 13, No. 15, No. 30, and No. 31) other than the strain No. 19 vigorously proliferated at a salinity concentration of 12 w/v % and proliferated predominantly as compared to the salt-tolerant *Staphylococcus* bacteria. Further, the same results were also obtainable even at a salinity concentration of 14 to 18 w/v %. As described above, it was found that the salt-tolerant *Lactobacillus* of the present invention could culture the salt-tolerant *Lactobacillus* well at a salinity concentration of 12 to 18 w/v % and the salt-tolerant *Lactobacillus* could be preferentially cultured even when about 1 v/v % salt-tolerant *Staphylococcus* bacteria was incorporated into the salt-tolerant *Lactobacillus*.

The salinity concentration of the medium is preferably 11 w/v % or more since it is more proliferative than bacteria such as the salt-tolerant *Staphylococcus* bacteria, and the like, which are assumed as bacteria (contaminated bacteria). Meanwhile, when the salinity concentration is 18 w/v %, the proliferation rate of the salt-tolerant *Lactobacillus* itself (2) Preparation of Spleen Cell Suspension:

Cells collected from the spleen of the experimental mouse (C57BL/6) were collected in a 1.5 mL reaction tube (manufactured by Greiner Bio-One), and 0.5 mL of erythrocyte lysis buffer (0.155M NH$_4$Cl, 0.01 M Tris-HCl, pH 7.5) was added to suspend the spleen cells. Thereafter, 0.5 mL of phosphate buffer (PBS) at pH 6.8 was added, and the mixture was centrifuged at 1200 rpm for 5 minutes and washed twice with a phosphate buffer (PBS) at pH 6.8.

The mixture was suspended in a basic medium to prepare a spleen cell suspension. Further, the same basic medium as in Example 1 was used. The number of cells of the obtained spleen cell suspension was calculated using a hemocytometer.

(3) Cell Culture:

The spleen cell suspension was adjusted with the basic medium so as to be $2 \times 10^6$ cells/mL, and 3 mL of the adjusted spleen cell suspension was seeded in a 6-well microplate (manufactured by Falcon Corporation) to obtain $6 \times 10^6$ cells/3 mL/well. Thereafter, 30 μL, of each *Lactobacillus* suspension (1 mg/mL) was added and cultured at 37° C. and 5% $CO_2$ for 2 days, thereby obtaining a *Lactobacillus*-added cultured product. In addition, a *Lactobacillus* suspension was obtained by culturing the spleen cell suspension without adding bacterial cells (*Lactobacillus* suspension) under the same condition (37° C., 5% $CO_2$) as the level to which the cells were added, and determined as a control group.

(4) Measurement of Cytokine:

After culturing for 42 hours in the culture for 2 days, 2 μL of BD GolgiStop (trademark) (manufactured by Nippon Becton Dickinson Company, Ltd) was added to each culture and mixed. Then, the culture was further cultured for 6 hours under the condition of 37° C. and 5% $CO_2$ (total culturing time 48 hours). Thereafter, the cultured cell culture liquid was transferred to a 15 mL conical tube (manufactured by Nippon Becton Dickinson Company, Ltd), centrifuged at 1200 rpm for 5 minutes, and the cells were collected. Thereafter, the collected cells were subjected to fixing/permeation operation using a BD Cytofix/Cytoperm (trademark) Fixation/Permeabilization Kit (manufactured by Nippon Becton Dickinson Company, Ltd). Operation was performed in accordance with the attached instructions.

Here, for convenience of the antibody to be used, the cells were divided into two groups, i.e., a first group confirming the cells producing interleukin-22 and the cells producing interferon-γ and a second group confirming the cells producing interleukin-10, and stained.

In the first group, PE labeled anti-interleukin-22 antibody (manufactured by affymetrix eBioscience), Alexa 647-labeled anti-interferon-γ antibody (manufactured by BD Pharmingen), and violetFluor 450-labeled anti-B220 antibody (manufactured by TONBO Biosciences) were used.

In the second group, PE-labeled anti-interleukin-10 antibody (manufactured by BioLegend, Inc), Alexa 647-labeled anti-interferon-γ antibody (manufactured by BD Pharmingen), and violetFluor 450-labeled anti-B220 antibody (manufactured by TONBO Biosciences) were used.

Figure 15:
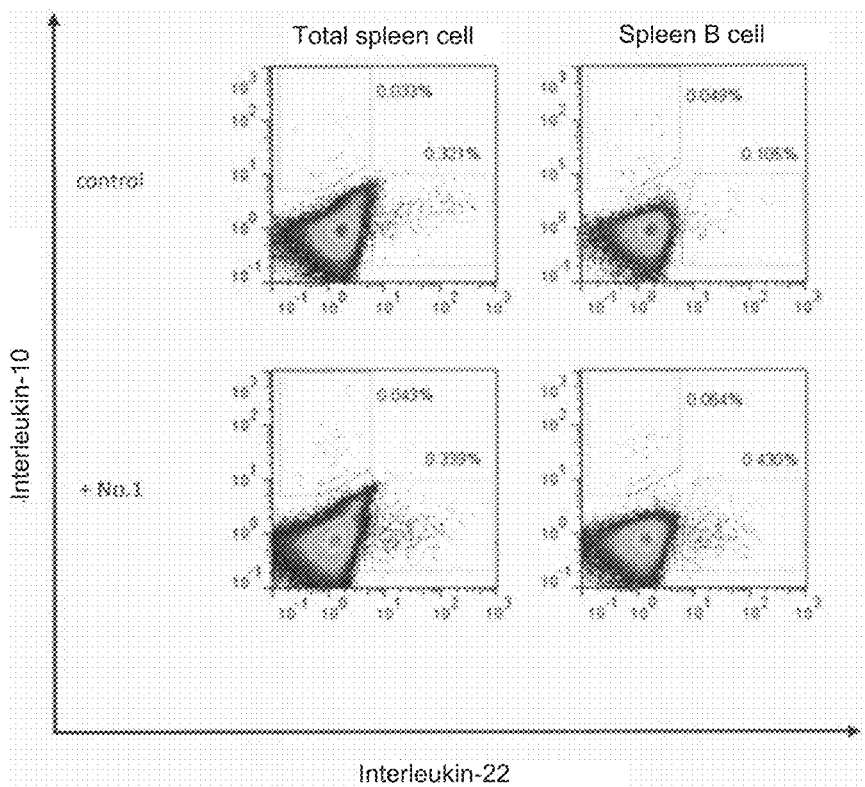
FIG. 15 is a diagram showing results of flow cytometry in Example 5.
Figure 16:
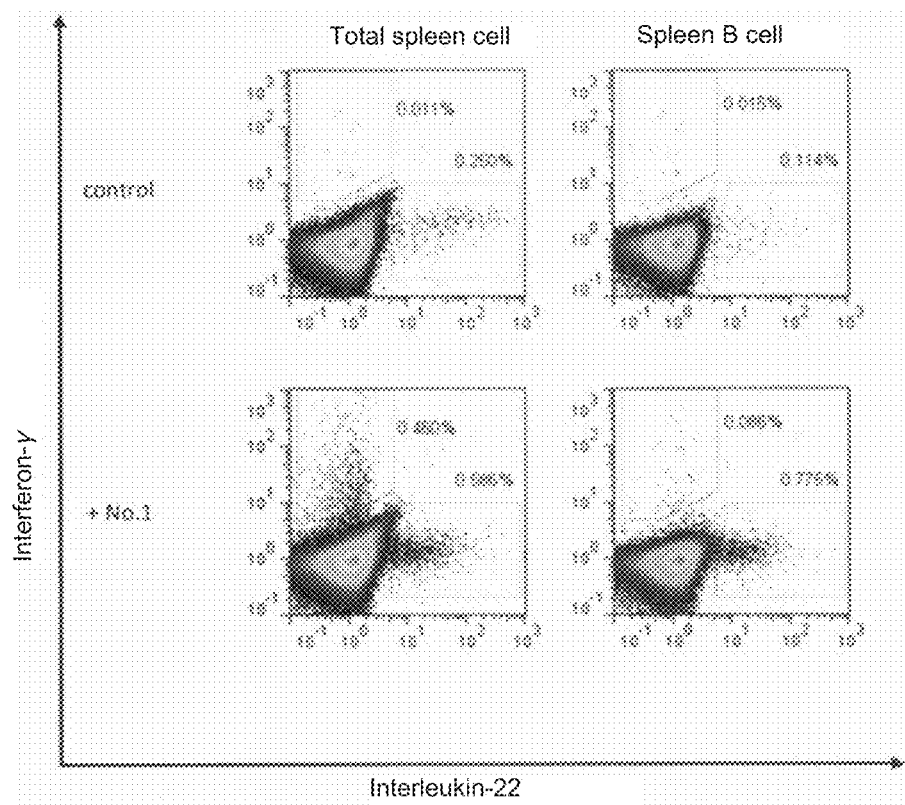
FIG. 16 is a diagram showing results of flow cytometry in Example 5.
Figure 17:
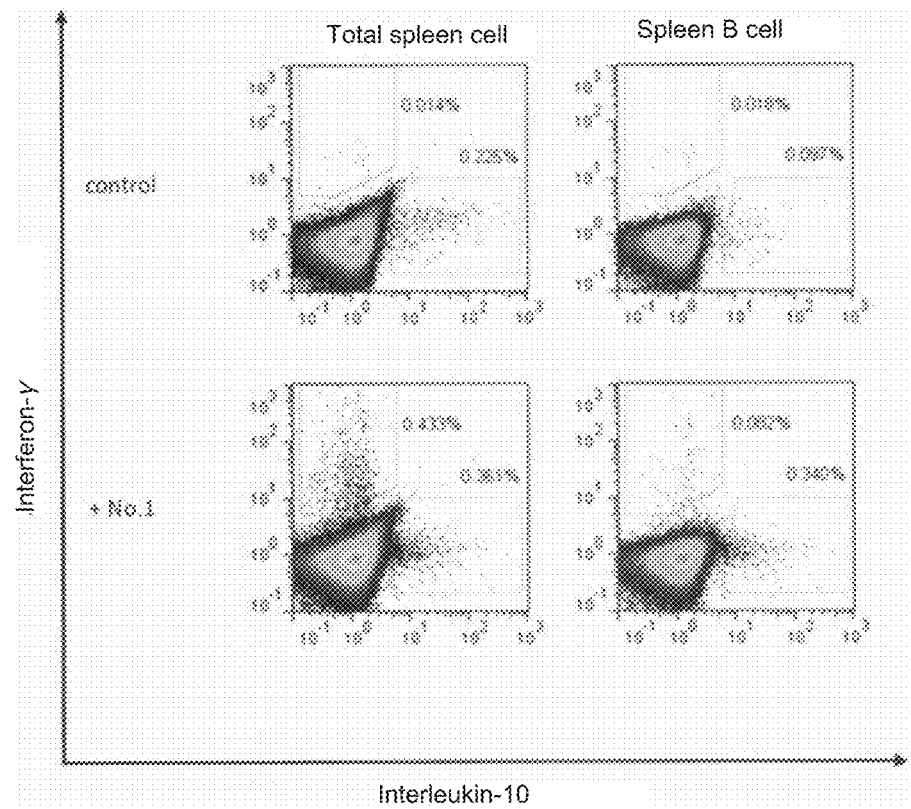
FIG. 17 is a diagram showing results of flow cytometry in Example 5.

In addition, as shown in FIG. 15, when cells producing interleukin-22 and cells producing interleukin-10 were simultaneously detected, the PE-labeled anti-interleukin-22 antibody (manufactured by affymetrix eBioscience), the Alexa 647-labeled anti-interleukin-10 antibody (manufactured by BD Pharmingen), and the violetFluor 450-labeled anti-B220 antibody (manufactured by TONBO Biosciences) were used (third group). In FIGS. 15 to 17, results of cell staining for each of the cells before staining divided into three groups (the first group to the third group) are shown.

After staining, the mixture was centrifuged at 1200 rpm for 5 minutes, and the cells were collected, suspended in 0.5 mL of phosphate buffer (PBS) at pH 6.8, and determined as a sample for measurement.

Cytokine measurement was performed using flow cytometry (MACSQuant Analyzer manufactured by Miltenyi Biotech). In addition, for analysis, FCS data analysis software FlowJo (manufactured by FlowJo, LLC) was used.

(5) Measurement of Cytokine-Producing Cell Amount:

(5-1) Interleukin-22-Producing Cell Amount:

With respect to the analysis results of *Lactobacillus*-added cultured product obtained by flow cytometry, the proportion of interleukin-22 positive cells in lymphocytes of total spleen cells was determined. In addition, the proportion of interleukin-22 positive cells in B220 positive cells (spleen B cells) was determined.

Figure 8:
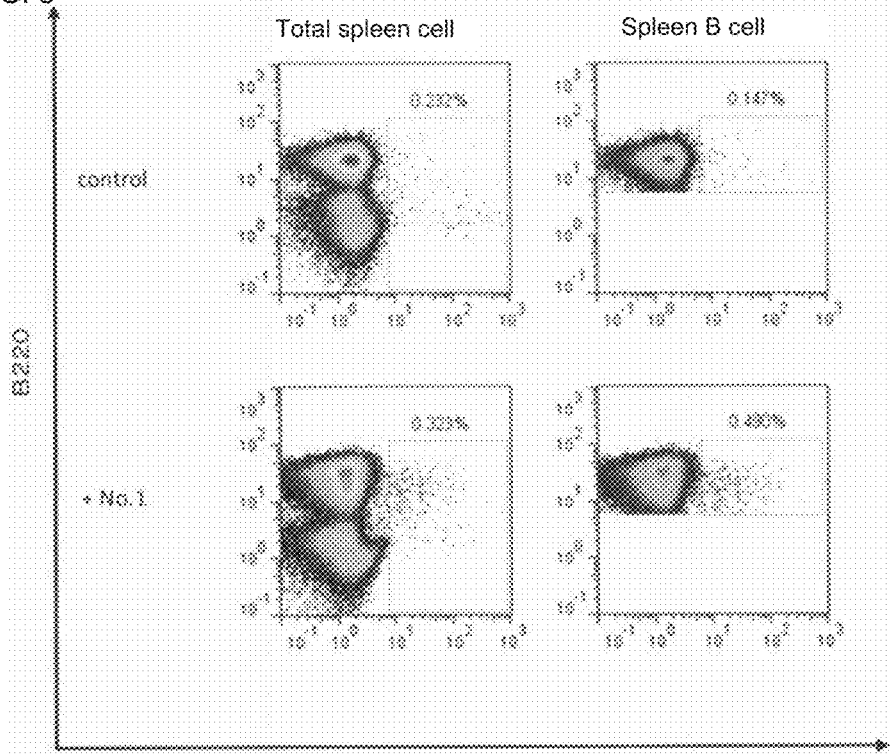
FIG. 8 is a diagram showing results of flow cytometry in Example 5.

Further, with respect to the analysis result of the control group obtained by flow cytometry (group obtained by culturing without addition of the *Lactobacillus* suspension), the proportion of the interleukin-22 positive cells in total spleen cells was determined in the same manner as in the case of the *Lactobacillus*-added cultured product. Further, the proportion of interleukin-22 positive cells in B220 positive cells in the control group was determined. In addition, in FIG. 8, an example of measurement in flow cytometry is shown, wherein the vertical axis indicates expression of B220 and the horizontal axis indicates expression of interleukin-22. In the upper part of FIG. 8, the control group (control) is shown, and in the lower part of FIG. 8, a case where the strain No. 1 is added (indicated as "+No. 1") is shown. Further, a proportion of interleukin-22 positive cells in lymphocytes of the total spleen cells is shown on the left side in FIG. 8 and a proportion of interleukin-22 positive cells in B220 positive cells (spleen B cells) is shown on the right side in FIG. 8.

Further, the "proportion of interleukin-22 positive cells in all spleen cells" when the value calculated from the control group was determined as the reference (100) was calculated, and the calculated value was determined as an interleukin-22-producing cell amount in total spleen cells (IL-22$^+$/total spleen cells). Similarly, the "proportion of interleukin-22 positive cells in B220 positive cells" when the value calculated from the control group was determined as the reference (100) was calculated, and the calculated value was determined as an interleukin-22-producing cell amount in spleen B cells (IL-22$^+$/spleen B cells). Further, the test was repeatedly performed to obtain the mean value (X$^-$) and the standard error (S.E.). In the present Example, "mean value (X$^-$)" is a mean value of six tests (n=6).

Figure 9:
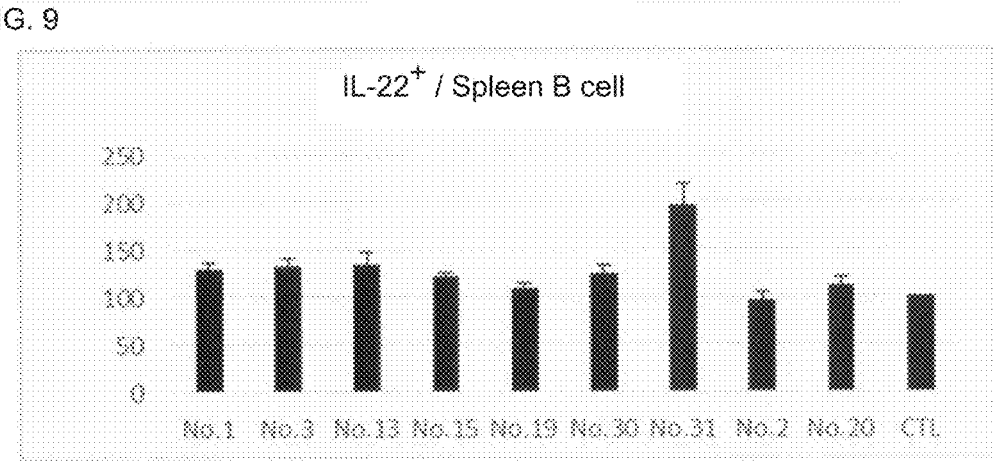
FIG. 9 is a graph showing results of a measurement test of interleukin-22 in Example 5.

Results with respect to the interleukin-22-producing cell amount in spleen B cells (IL-22$^+$/spleen B cells) are shown in FIG. 9 and Table 6 ("Spleen B Cells" in "IL-22-Producing Cell Amount"). In addition, in FIG. 9, "IL-22+/spleen B cell" shows the producing cell amount of interleukin-22 among B cells of spleen cells (IL-22$^+$/spleen B cell).

Figure 10:
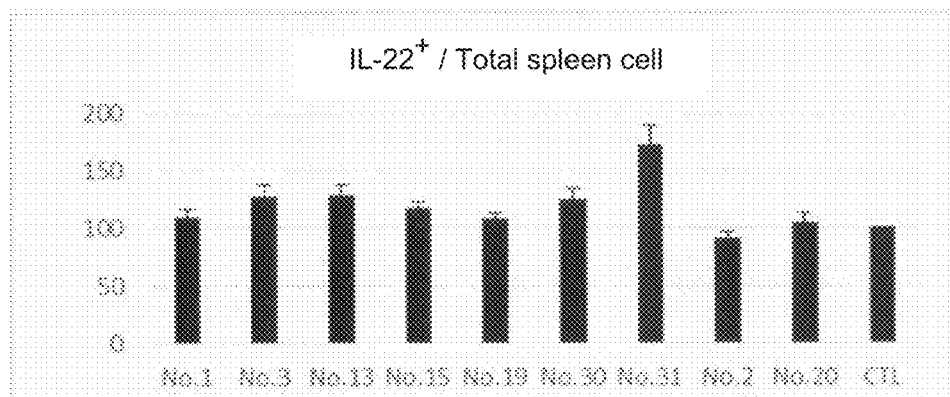
FIG. 10 is a graph showing results of the measurement test of interleukin-22 in Example 5.

Results with respect to the interleukin-22-producing cell amount in spleen cells (IL-22$^+$/total spleen cells) are shown in FIG. 10 and Table 6 ("Total Spleen Cells" in "IL-22-Producing Cell Amount"). In FIG. 10, "IL-22$^+$/Total spleen cells" shows the producing cell amount of interleukin-22 among spleen cells (IL-22$^+$/total spleen cells).

TABLE 6-1

|  |  | Strain No. | x$^-$ | S.E. |
|---|---|---|---|---|
| IL-22-Producing Amount | Spleen B Cell | No.1 | 128 | 9 |
|  |  | No.3 | 132 | 10 |
|  |  | No.13 | 133 | 13 |
|  |  | No.15 | 120 | 5 |
|  |  | No.19 | 109 | 5 |
|  |  | No.30 | 123 | 10 |
|  |  | No.31 | 196 | 24 |
|  |  | No.2 | 96 | 8 |
|  |  | No.20 | 111 | 9 |
|  |  | control | 100 | — |
|  | Total Spleen Cell | No.1 | 109 | 8 |
|  |  | No.3 | 127 | 11 |
|  |  | No.13 | 128 | 11 |
|  |  | No.15 | 116 | 7 |
|  |  | No.19 | 107 | 5 |
|  |  | No.30 | 124 | 10 |
|  |  | No.31 | 172 | 18 |
|  |  | No.2 | 90 | 6 |
|  |  | No.20 | 104 | 9 |
|  |  | control | 100 | — |
| IL-10-Producing Amount | Spleen B Cell | No.1 | 407 | 79 |
|  |  | No.3 | 142 | 12 |
|  |  | No.13 | 134 | 13 |
|  |  | No.15 | 127 | 14 |
|  |  | No.19 | 111 | 6 |

TABLE 6-1-continued

|  |  | Strain No. | x⁻ | S.E. |
|---|---|---|---|---|
|  |  | No.30 | 148 | 12 |
|  |  | No.31 | 292 | 15 |
|  |  | No.2 | 120 | 8 |
|  |  | No.20 | 138 | 15 |
|  |  | control | 100 | — |
|  | Total Spleen Cell | No.1 | 374 | 67 |
|  |  | No.3 | 146 | 7 |
|  |  | No.13 | 142 | 5 |
|  |  | No.15 | 127 | 10 |
|  |  | No.19 | 115 | 7 |
|  |  | No.30 | 154 | 6 |
|  |  | No.31 | 309 | 22 |
|  |  | No.2 | 106 | 7 |
|  |  | No.20 | 140 | 10 |
|  |  | control | 100 | — |
| IFN-γ-Producing Amount | Spleen B Cell | No.1 | 151 | 19 |
|  |  | No.3 | 265 | 24 |
|  |  | No.13 | 254 | 26 |
|  |  | No.15 | 220 | 26 |
|  |  | No.19 | 247 | 48 |
|  |  | No.30 | 252 | 32 |
|  |  | No.31 | 305 | 39 |
|  |  | No.2 | 192 | 21 |
|  |  | No.20 | 189 | 20 |
|  |  | control | 100 | — |
|  | Total Spleen Cell | No.1 | 168 | 43 |
|  |  | No.3 | 428 | 46 |
|  |  | No.13 | 389 | 50 |
|  |  | No.15 | 289 | 41 |
|  |  | No.19 | 274 | 82 |
|  |  | No.30 | 290 | 41 |
|  |  | No.31 | 545 | 117 |
|  |  | No.2 | 307 | 20 |
|  |  | No.20 | 329 | 23 |
|  |  | control | 100 | — |

Figure 11:
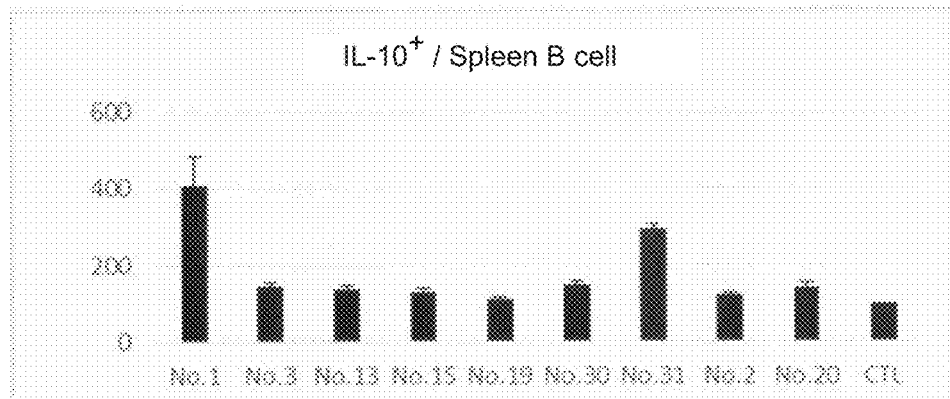
FIG. 11 is a graph showing results of a measurement test of interleukin-10 in Example 5.
Figure 12:
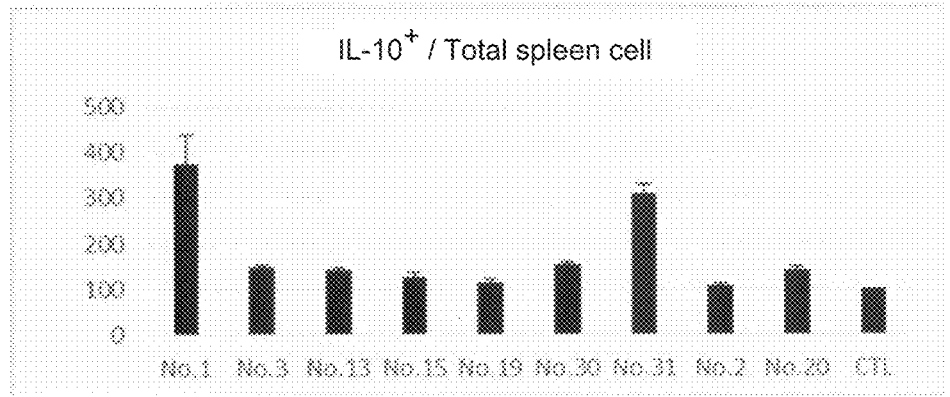
FIG. 12 is a graph showing results of the measurement test of interleukin-10 in Example 5.

(5-2) Interleukin-10-Producing Cell Amount:

The "interleukin 10-producing cell amount" was also calculated in the same manner as the measurement of the "interleukin 22-producing cell amount". Results of the interleukin-10-producing cell amount in B cells of spleen cells are shown in FIG. 11 and Table 6, and results of the interleukin-10-producing cell amount in spleen cells are shown in FIG. 12 and Table 6. Further, in Table 6, results of the interleukin-10-producing cell amount in B cells of spleen cells are shown in the column "Spleen B Cells" of "IL-10-producing cell amount", and results of the interleukin-10-producing cell amount in spleen cells are shown in the column "Total Spleen Cells" of "IL-10-producing amount".

In addition, in FIG. 11, "IL-10⁺/spleen B cell" shows the producing cell amount of interleukin-10 among B cells of spleen cells. In FIG. 12, "IL-10⁺/total spleen cells" shows the producing cell amount of interleukin-10 among spleen cells.

Figure 13:
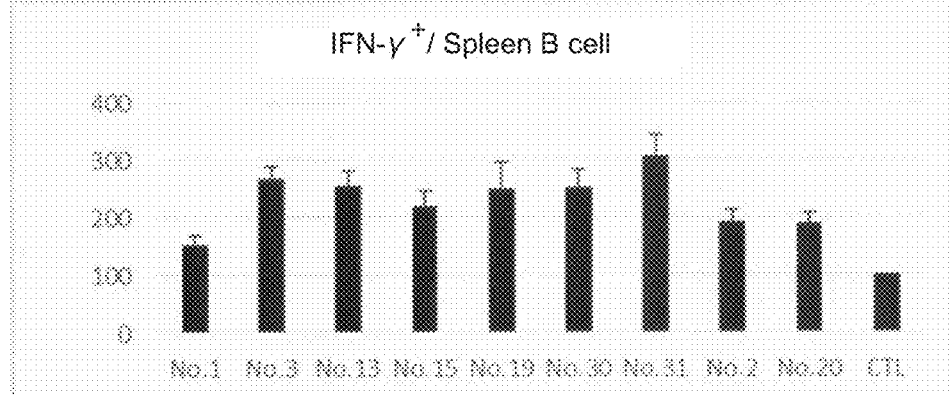
FIG. 13 is a graph showing results of a measurement test of interferon-γ in Example 5.
Figure 14:
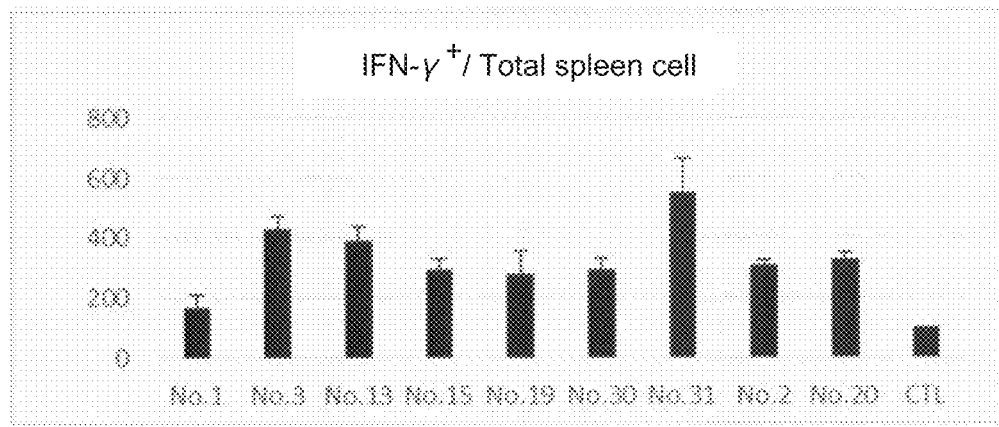
FIG. 14 is a graph showing results of the measurement test of interferon-γ in Example 5.

(5-3) Interferon-γ-Producing Cell Amount:

The "interferon-γ-producing cell amount" was also calculated in the same manner as the measurement of the "interleukin-22-producing cell amount". Further, results of the interferon-γ-producing cell amount in B cells of spleen cells are shown in FIG. 13 and Table 6, and results of the interferon-γ-producing cell amount in spleen cells are shown in FIG. 14 and Table 6. Further, in Table 6, results of the interleukin-22-producing cell amount in B cells of spleen cells are shown in the column "Spleen B Cells" of "IFN-γ-producing cell amount", and results of the interleukin-22-producing cell amount in spleen cells are shown in the column "Total Spleen Cells" of "IFN-γ-producing amount".

In FIG. 13, "IFN-γ⁺/spleen B cell" shows the producing cell amount of interferon-γ among B cells of spleen cells. In FIG. 14, "IFN-γ⁺/total spleen cells" shows the producing cell amount of interferon-γ among spleen cells.

From the above results, it could be appreciated that when the representative strains (Nos. 1, 3, 13, 15, 19, 30, and 31) and spleen cells were co-cultured, the proportions of B cells producing interleukin-22, interleukin-10, and interferon-γ increased as compared to the control group (group cultured without addition of *Lactobacillus* suspension) (see FIGS. 9, 11, and 13). In addition, it could be appreciated that the proportions of cells producing interleukin-22, interleukin-10, and interferon-γ increased by these representative strains not only in B cells but also in total spleen cells (see FIGS. 10, 12, and 14).

Further, in the DNA microarray analysis of Example 3, it was shown that the production of interleukin-22, interleukin-10, and interferon-γ was induced in B cells by the strain No. 1 which is the representative strain. In addition, in the present Example, a measurement test of cytokine was performed in cell culture in vitro. As a result, it could be confirmed that the production of interleukin-22, interleukin-10, and interferon-γ was induced in all of the representative strains without being limited to the strain No. 1. Specifically, it could be appreciated that production of interleukin-22, interleukin-10, and interferon-γ was induced among spleen cells including B cells, and the amount of cells producing cytokines increased to about 1.1 to 5 times by co-culturing with the above-described representative strains which were salt-tolerant lactobacilli (see FIGS. 9 to 14 and Table 6).

(Subset of B Cell)

FIGS. 15 to 17 show flow cytometry analysis results of cytokine production of lymphocytes of total spleen cells and spleen B cells (B220 positive (B220⁺)) cells. Specifically, FIG. 15 shows results of development with interleukin-22 and interleukin-10, FIG. 16 shows results of development with interleukin-22 and interferon-γ, and FIG. 17 shows result of development with interleukin-10 and interferon-γ, respectively.

As shown in FIGS. 15 to 17, even in any case of the total spleen cells and the spleen B cells (B220 positive (B220⁺) cells), cells producing two or more among interleukin-22, interleukin-10, and interferon-γ could not be confirmed. In other words, one cell was found to produce only one kind of interleukin-22, interleukin-10, and interferon-γ.

Further, FIGS. 15 to 17 show the results obtained by adding the strain No. 1. However, even in any case of the specimen including the representative strain, the same results as those of the strain No. 1 could be obtained.

Here, it is known that a helper T cell has a subset (subpopulation) classified according to the characteristics of cytokine production. Specifically, it is known that the helper T cell includes cells that have the role of producing different cytokines, such as, Th1 cell (characterized by producing interferon-γ), Th2 cell (characterized by producing interleukin-4), Th9 cell (characterized by producing interleukin-9), Th17 cell (characterized by producing interleukin-17), Th22 cell (characterized by producing interleukin-22), and the like.

Meanwhile, it is not known whether or not there is a subset for B cells, but from the results in FIGS. 15 to 17, it could be appreciated that there is a subset for B cell as in the helper T cell. In other words, it could be confirmed that there are "B cell producing interleukin-22", "B cell producing interleukin-10", and "B cell producing interferon-γ", respectively, in B cells. A regulatory B cell among B cells is known to produce interleukin-10. Among them, the "B cell producing interleukin-10" is considered to be a regulatory B cell, and the regulatory B cell is also considered to be increased or activated by these lactobacilli.

In addition, in the control group (group cultured without addition of *Lactobacillus* suspension), B cells producing interleukin-22, interleukin-10, and interferon-γ were detected even though amounts thereof were very small. As a result, it could be appreciated that B cells produced the cytokines (interleukin-22, interleukin-10, and interferon-γ) even under general conditions (culture conditions not containing *Lactobacillus*).

In the present Example, B220 positive cells were detected and analyzed for B cells, but similar to the analysis case in the CD19 positive cells instead of B220 positive cells, cells producing interleukin-22, interleukin-10, and interferon-γ were detected. From these results, it could be appreciated that the B cell produced the cytokine, and the production of the cytokine was induced by the representative strain.

Example 6

(Feeding Test of *Lactobacillus*)

Bacterial cells of sterilized *Lactobacillus* were fed to experimental mice (C57BL/6), and serum IgA in the blood of the mice was measured thereafter. As the *Lactobacillus*, among the representative strains, the strains No. 1 and No. 30 were used.

(1) Preparation of *Lactobacillus* Mixed Feed:

A feed was prepared by containing 1 (w/w) % bacterial cells of *Lactobacillus* that were sterilized and then lyophilized in a general feed for mouse. Further, as the general feed for mouse, a mouse breeding feed CE-2 (manufactured by CLEA Japan, Inc.) was used.

(2) Feed Test:

Six general experimental mice (C57BL/6) (8-week-old female) were divided into two groups, wherein one group was fed with the *Lactobacillus* mixed feed (*Lactobacillus* administered group) and the other group was fed with general feed for mouse not containing bacterial cells of *Lactobacillus* (control group: *Lactobacillus* non-administered group), and they are bred. Blood from each of the mice was collected after 14 days from the start of the test and serum was collected by centrifugation and prepared.

(3) Measurement of IgA:

The total IgA concentration in the prepared serum was measured by an ELISA method.

For the measurement, a MICROLON 96 well microplate (manufactured by Greiner Bio-One) was used. A goat anti-mouse IgA-UNLB antibody (manufactured by Southern Biotech) was used as an antigen, a goat anti-mouse IgA-AP conjugate (manufactured by Southern Biotech) was used as a secondary antibody, an alkaline phosphatase substrate (manufactured by SIGMA) was used as a chromogenic substrate. In addition, a Vmax Kinetic Microplate Reader (manufactured by Molecular Devices) was used for measurement of absorbance (405 nm). Here, calibration curves of absorbance and IgA concentration were prepared using specimens of a serial diluted control group. Then, using this calibration curve, IgA concentrations for specimens in the *Lactobacillus*-administered group and in the control group (*Lactobacillus* non-administered group) were calculated. Thereafter, the relative value of the IgA concentration of each specimen was determined using the mean value of IgA concentration in the control group (*Lactobacillus* non-administered group) as a reference value (100).

For each numerical value of the *Lactobacillus*-administered group and the control group (*Lactobacillus* non-administered group), F test was performed to check whether or not there was a significant difference in dispersion. After that, Student's t test (this is a two—sample test assuming equal variance) was performed.

As a result, as shown in Tables 7 and 8, FIGS. 18 and 19, in the *Lactobacillus*-administered groups of the strain No. 1 and the strain No. 30, the IgA concentration in the serum was about 25% and about 22% higher than that of the control group (*Lactobacillus* non-administered group), respectively. In addition, the results of Student's t test were p<0.05 (p=0.038) and p<0.01 (p=0.0001), respectively, and the significant difference was admitted at the significance level of 5% and 1%. From these results, it could be appreciated that the total IgA concentration in the serum increased by the intake of the salt-tolerant *Lactobacillus* of the present invention and the immunostimulatory potency increased by the salt-tolerant *Lactobacillus* of the present invention.

TABLE 7

|  | Control Group | *Lactobacillus*-administered Group (No. 1) |
| --- | --- | --- |
| Mean Value ($x^-$) | 100.0 | 125.0 |
| Standard Deviation | 9.1 | 7.3 | p = 0.038

TABLE 8

|  | Control Group | *Lactobacillus*-administered Group (No. 30) |
| --- | --- | --- |
| Mean Value ($x^-$) | 100.0 | 122.3 |
| Standard Deviation | 1.9 | 1.1 | p = 0.0001

From the above, as shown in Tables 1 to 3, it could be appreciated that the salt-tolerant *Lactobacillus* of the present invention could improve the viability and activation potency of B cells by directly acting on B cells, and further, could improve the viability and activation potency of T cells. From these facts, it could be appreciated that the salt-tolerant *Lactobacillus* of the present invention could have an immunostimulatory action. Further, it could be appreciated that the strain No. 1 among the salt-tolerant lactobacilli of the present invention induced production of interleukin-22, interleukin-10, and interferon-γ. In addition, as shown in Table 6, it could be appreciated that the strains Nos. 3, 13, 15, 19, 30, and 31 other than the strain No. 1 induced production of interleukin-22, interleukin-10, and interferon-γ. Further, it is thought that the salt-tolerant lactobacilli of the representative strains increase the total IgA concentration in the serum, and the immunostimulatory potency increases by these lactobacilli (see Tables 7 and 8, FIGS. 18 and 19). Further, as shown in Tables 4 and 5, it could be appreciated that when the salinity concentration was 11 to 18 w/v %, the salt-tolerant *Lactobacillus* of the present invention could be selectively and well cultured, and the proliferation of contaminated bacteria could be inhibited.

INDUSTRIAL APPLICABILITY

The salt-tolerant *Lactobacillus* of the present invention may be employed as an active ingredient of an immunostimulant that exerts an immunostimulatory action by being added to foods and drinks, supplements, pharmaceuticals, and the like or may be foods and drinks, supplements, pharmaceuticals, and the like. The method of culturing a salt-tolerant *Lactobacillus* of the present invention may be employed as the method of culturing a salt-tolerant *Lactobacillus* of the present invention. The immunostimulant of the present invention may be employed as an immunostimulant that exerts an immunostimulatory action by being added to foods and drinks, supplements, pharmaceuticals, and the like or may be foods and drinks, supplements, pharmaceuticals, and the like. The food and drink, for example, may include processed seasoning of materials for miso, instant miso soup, cooked miso (processed miso), name-miso such as kinzanji miso, soy sauce, soup, season sauce, seasoning sauce, pickle (lightly-pickled), and the like, seasoning foods of materials for rice, or the like, side dishes, sweet rice drinks (yeast drinks), sweet red-bean porridge, and the like.

Accession Number

Accession number NITE BP-02318, Accession number NITE BP-02319, Accession number NITE BP-02320, Accession number NITE BP-02321, Accession number NITE BP-02322, Accession number NITE BP-02323, and Accession number NITE BP-02324 a salt-tolerant *lactobacillus* of Accession number NITE BP-02320, a salt-tolerant *lactobacillus* of Accession number NITE BP-02321, a salt-tolerant *lactobacillus* of Accession number NITE BP-02322, a salt-tolerant *lactobacillus* of Accession number NITE BP-02323, and a salt-tolerant *lactobacillus* of Accession number NITE BP-02324.

2. The salt-tolerant *lactobacillus* according to claim 1, wherein the salt-tolerant *lactobacillus* is isolated in a brewing process of miso.

3. The salt-tolerant *lactobacillus* according to claim 1, wherein production of interleukin-22, interleukin-10, and interferon-y is induced.

---

---

The invention claimed is:

1. A salt-tolerant *lactobacillus* having an immunostimulatory action with viability and activation potency of B cells selected from the group consisting of the following:

a salt-tolerant *lactobacillus* of Accession number NITE BP-02318, a salt-tolerant *lactobacillus* of Accession number NITE BP-02319, 4. A method of culturing a salt-tolerant *lactobacillus* in which the salt-tolerant *lactobacillus* according to claim 1 is cultured in a medium having a salinity concentration of 11 to 18 w/v %.

5. An immunostimulant comprising the salt-tolerant *lactobacillus* according to claim 1.

* * * * *

UNITED STATES PATENT AND TRADEMARK OFFICE
CERTIFICATE OF CORRECTION

PATENT NO. : 11,260,085 B2
APPLICATION NO. : 16/332577
DATED : March 1, 2022
INVENTOR(S) : Toshihiko Kumazawa et al.

It is certified that error appears in the above-identified patent and that said Letters Patent is hereby corrected as shown below:

In the Claims

At Column 38, Claim 3, text Line 18, "interferon-y" should read - interferon-$\gamma$ -

Signed and Sealed this
Seventh Day of June, 2022

Katherine Kelly Vidal
*Director of the United States Patent and Trademark Office*

SEQUENCE LISTING

<160> NUMBER OF SEQ ID NOS: 1

<210> SEQ ID NO 1
<211> LENGTH: 1000
<212> TYPE: DNA
<213> ORGANISM: Staphylococcus saprophyticus subsp. saprophyticus

<400> SEQUENCE: 1

```
gggcaatgcg ggtgctatac atgcagtcga gcgaacagat aaggagcttg ctcctttgac      60
gttagcggcg gacgggtgag taacacgtgg gtaacctacc tataagactg ggataacttc     120
gggaaaccgg agctaatacc ggataacatt tggaaccgca tggttctaaa gtgaaagatg     180
gttttgctat cacttataga tggacccgcg ccgtattagc tagttggtaa ggtaacggct     240
taccaaggca acgatacgta gccgacctga gagggtgatc ggccacactg gaactgagac     300
acggtccaga ctcctacggg aggcagcagt agggaatctt ccgcaatggg cgaaagcctg     360
acggagcaac gccgcgtgag tgatgaaggg tttcggctcg taaaactctg ttattaggga     420
agaacaaatg tgtaagtaac tgtgcacatc ttgacggtac ctaatcagaa gccacggct      480 aactacgtgc cagcagccgc ggtaatacgt aggtggcaag cgttatccgg aattattggg     540
cgtaaagcgc gcgtaggcgg tttcttaagt ctgatgtgaa agcccacggc tcaaccgtgg     600
agggtcattg gaaactggga aacttgagtg cagaagagga aagtggaatt ccatgtgtag     660
cggtgaaatg cgcagagata tggaggaaca ccagtggcga aggcgacttt ctggtctgta     720
actgacgctg atgtgcgaaa gcgtggggat caaacaggat tagataccct ggtagtccac     780
gccgtaaacg atgagtgcta agtgttaggg ggtttccgcc ccttagtgct gcagctaacg     840
cattaagcac tccgcctggg gagtacgacc gcaaggttga aactcaaagg aattgacggg     900
gacccgcaca gcggtggag catgtggttt aattcgaagc aacgcgaaga accttaccaa      960
atcttgacat cctttgaaaa ctctagagat agagccttcc                          1000
```